US006114141A

United States Patent [19]
Dropulić et al.

[11] Patent Number: 6,114,141
[45] Date of Patent: *Sep. 5, 2000

[54] METHODS TO EXPRESS GENES FROM VIRAL VECTORS

[75] Inventors: Boro Dropulić, Ellicott City; Paula M. Pitha, Baltimore, both of Md.

[73] Assignee: The Johns Hopkins University School of Medicine, Baltimore, Md.

[ * ] Notice: This patent is subject to a terminal disclaimer.

[21] Appl. No.: 09/251,085

[22] Filed: Feb. 16, 1999

Related U.S. Application Data

[62] Division of application No. 08/917,625, Aug. 22, 1997, Pat. No. 5,888,767, which is a division of application No. 08/758,598, Nov. 27, 1996, Pat. No. 5,885,806
[60] Provisional application No. 60/032,800, Nov. 28, 1995.
[51] Int. Cl.$^7$ ............................ C12N 15/63; C12N 15/67; C12N 15/86
[52] U.S. Cl. ................. 435/69.1; 435/91.31; 435/320.1; 435/457; 514/44; 536/24.5
[58] Field of Search ................................ 435/69.1, 91.31, 435/320.1, 325, 375, 455, 456, 457; 514/44; 536/24.5

[56] References Cited

U.S. PATENT DOCUMENTS

| | | |
|---|---|---|
| 5,144,019 | 9/1992 | Rossi et al. . |
| 5,180,818 | 1/1993 | Cech et al. . |
| 5,225,337 | 7/1993 | Robertson et al. . |
| 5,272,262 | 12/1993 | Rossi et al. . |
| 5,888,767 | 3/1999 | Dropulic et al. ................... 435/69.1 |

FOREIGN PATENT DOCUMENTS

| | | |
|---|---|---|
| 52803/93 | 7/1994 | Australia . |
| 0 612 844 A2 | 8/1994 | European Pat. Off. . |
| 0 653 488 A1 | 5/1995 | European Pat. Off. . |
| WO 93/23569 | 11/1993 | WIPO . |
| WO 94/01549 | 1/1994 | WIPO . |
| WO 94/26877 | 11/1994 | WIPO . |
| WO 95/29241 | 11/1995 | WIPO . |
| WO 95/30755 | 11/1995 | WIPO . |

OTHER PUBLICATIONS

Adachi et al., *J. Virol.*, 59, 284–291 (1986).
Altman, *Proc. Natl. Acad. Sci.*, 90, 10898–10900 (1993).
Anderson, *Science*, 256, 808–813 (1992).
Baltimore, *Nature*, 325, 395–396 (1988).
Barr et al., *Methods: A Companion to Methods in Enzymology*, 4, 169–176.
Benson, et al., *J. Exp. Med.*, 177, 1561–1566 (1993).
Buchschacher, Jr., et al., *J. Virol.*, 66, 2731–2739 (1992).
Buchschacher, Jr. et al., *Human Gene Ther.*, 3, 391–397 (1992).
Buchschacher, Jr., *JAMA*, 269, 2880–2886 (1993).
Carroll et al., *J. Virol.*, 68, 6047–6051 (1994).
Cech, *Science*, 236, 1532–1539 (1987).
Chen et al., *Nuc. Acids Res.*, 20, 4581–4589 (1992).
Chen et al., *Annals New York Academy of Sciences*, 660, 271–273 (1992).
Coffin, *Curr. Top. Microbiol. Immunol.*, 176, 143–164 (1992).
Coffin, *Science*, 267, 483–489 (1995).
Cohen, *Science*, 268, 1566 (1995).
Coombs et al., *New Engl. J. Med.*, 321, 1626–1631 (1989).
Cournoyer et al., *Ann. Rev. Immunol.*, 11, 297–329 (1993).
Dropulic et al., *J. Virol.*, 66, 1432–1441 (1992).
Dropulic et al., *Methods: A Companion to Methods in Enzymology*, 5, 43–49 (1993).
Dropulic et al., *Antisense Research and Development*, 3, 87–94 (1993).
Dropulic et al., *Human Gene Ther.*, 5, 927–939 (1994).
Dropulic et al., *Gene Therapy and Molecular Medicine*, Abst. No. C6–310, 391 (Mar. 26–Apr. 1, 1995).
Freed et al., *Proc. Natl. Acad. Sci.*, 89, 70–74 (1992).
Friedmann, *Science*, 244, 1275–1281 (1989).
Gilboa et al., *TIG*, 10, 139–144 (1994).
Hampel et al., *Nuc. Acids Res.*, 18, 299–304 (1990).
Harada et al., *Science*, 563–566 (1985).
Haseloff et al., *Nature*, 334, 585–591 (1988).
Haseloff et al., *Gene*, 82, 43–52 (1989).
Ho et al., *New Engl. J. Med.*, 321, 1621–1625 (1989).
Ho et al., *Nature*, 373, 123–126 (1995).
Inoue et al., *Proc. Natl. Acad. Sci.*, 88, 2278–2282 (1991).
James et al., *Annals New York Academy of Sciences*, 660, 274–275 (1992).
Kim et al., *AIDS Res. & Hum. Restrovir.*, 9, 875–882 (1993).
Liska et al., *J. Gen. Virol.*, 75, 2955–2962 (1994).
Lusso et al., *J. Virol.*, 69, 3712–3720 (1995).
Malim et al., *J. Exp. Med.*, 176, 1197–1201 (1992).
Marasco et al., *Proc. Natl. Acad. Sci.*, 90, 7889–7893 (1993).
Matthews, *AIDS Res. & Hum. Retrovir.*, 10, 631–632 (1994).
Miller, *Nature*, 357, 455–460 (1992).
Mulligan, *Science*, 260, 926–931 (1993).
Myers et al., HIV Sequence Database, Los Alamos Natl. Lab., 1–A–9 to 1–A–17 (Sep. 1992).
Ojwang et al., *Proc. Natl. Acad. Sci.*, 89, 10802–06 (1992).
Page et al., *J. Virol.*, 64, 5270–5276 (1990).
Parolin et al., *J. Virol.*, 68, 3888–3895 (1994).

(List continued on next page.)

*Primary Examiner*—Robert A. Schwartzman
*Assistant Examiner*—Thomas G. Larson
*Attorney, Agent, or Firm*—Morrison & Foerster

[57] ABSTRACT

The present invention provides a conditionally replicating viral vector, methods of making, modifying, propagating and selectively packaging, and using such a vector, isolated molecules of specified nucleotide and amino acid sequences relevant to such vectors, a pharmaceutical composition and a host cell comprising such a vector, the use of such a host cell to screen drugs. The methods include the prophylactic and therapeutic treatment of viral infection, in particular HIV infection, and, thus, are also directed to viral vaccines and the treatment of cancer, in particular cancer of viral etiology. Other methods include the use of such conditionally replicating viral vectors in gene therapy and other applications.

34 Claims, 11 Drawing Sheets

OTHER PUBLICATIONS

Pathak et al., *Proc. Natl. Acad. Sci.,* 87, 6024–6028 (1990).
Pearson et al., *Proc. Natl. Acad. Sci.,* 87, 5079–5083 (1990).
Piatak et al., *Science,* 259, 1749–1754 (1993).
Poznansky et al., *J. Virol.,* 65, 532–536 (1991).
Preston et al., *Science,* 242, 1168–1171 (1988).
Richardson et al., *J. Virol.,* 67, 3997–4005 (1993).
Richardson et al., *J. Gen. Virol.,* 76, 691–696 (1995).
Roberts et al., *Science,* 242, 1171–1173 (1988).
Saag et al., *Nature,* 334, 440–444 (1988).
Saksela et al., *Proc. Natl. Acad. Sci.,* 91, 1104–1108 (1994).
Sarver et al., *Science,* 247, 1222–1225 (1990).
Sarver et al., *J. NTH Res.,* 5, 63–67 (1993).
Sarver et al., *AIDS Res. And Hum. Retrovir.,* 9, 483–487 (1993).
Stevenson et al., *Cell,* 53, 483–496 (1988).
Sullenger et al., *Cell,* 63, 601–608 (1990).
Sullenger et al., *Science,* 262, 1566–1569 (1994).
Sun et al., *Natl. Acad. Sci.,* 91, 9715–9719 (1994).
Symons, *Ann. Rev. Biochem.,* 61, 641–671 (1992).
Technology Access Report, "Ribozymes for Treating Hepatitis C", 17 (Feb. 1996).
Thierry et al., *Proc. Natl. Acad. Sci.,* 92, 9742–9746 (1995).
Travers et al., *Science,* 268, 1612–1615 (1995).
Uhlenbeck, *Nature,* 328, 596–600 (1987).
Weerasinge et al., *J. Virol.,* 65, 5531–5534 (1991).
Wei et al., *Nature,* 373, 117–122 (1995).
Winslow et al., *Virol.,* 196, 849–854 (1993).
Wu et al., *Cancer Res.,* 52, 3029–3034 (1992).
Yu et al., *Proc. Natl. Acad. Sci.,* 90, 6340–6344 (1993).
Yu et al., *Proc. Natl. Acad. Sci.,* 92, 699–703 (1995).
Yunoki et al., *Arch. Virol.,* 116, 143–158 (1991).
Zaia et al., *Annals New York Academy of Sciences,* 660, 95–106 (1992).
Zhou et al., *Gene,* 149, 33–39 (1994).

FIG; 1D

```
A  +105   GTGTGCCCGTCTG   +117
B                ...AC...

A  +118   TTGTGTGACTCTG   +130
B         .............

A  +131   GTAACTAGAGATC   +143
B         .C.G......A.
```

METHODS TO EXPRESS GENES FROM VIRAL VECTORS

This application is a divisional of U.S. Ser. No. 08/917,625 filed Aug. 22, 1997, now U.S. Pat. No. 5,888,767, which is a divisional of U.S. Ser. No. 08/758,598 filed Nov. 27, 1996, now U.S. Pat. No. 5,885,806; it is addressed to the elected subject matter in Ser. No. 08/758,598. These applications claim priority under 35 $USC_{119}$ from provisional patent application Ser. No. 60/032,800 which was converted from a regular application Ser. No. 08/563,459 filed Nov. 28, 1995. the contents of these applications are incorporated herein by reference.

TECHNICAL FIELD OF THE INVENTION

The present invention relates to a conditionally replicating viral vector, methods of making, modifying, propagating and selectively packaging such a vector, isolated molecules of specified nucleotide and amino acid sequences relevant to such vectors, a pharmaceutical composition and a host cell comprising such a vector, and methods of using such a vector and a host cell.

BACKGROUND OF THE INVENTION

The discovery of the human immunodeficiency virus (HIV) as the cause of acquired immune deficiency syndrome (AIDS) has fostered a plethora of research into the underlying mechanisms of the viral infectious cycle and viral pathogenesis. Studies on these mechanisms have provided researchers with an ever-increasing number of targets for the development of antiviral agents effective not only against HIV, but against other viruses as well. These antiviral agents, particularly those directed against HIV, can be categorized into groups depending on their mode of action. Such groups include inhibitors of reverse transcriptase, competitors of viral entry into cells, vaccines, and protease inhibitors, as well as a more recent group referred to herein as "genetic antiviral agents."

Generally, each type of antiviral agent has its own associated benefits and limitations, and must be assessed in terms of the exigencies of the particular treatment situation. Antiviral agents, such as zidovudine (3'-azido-3'-deoxythymidine, also known as AZT), protease inhibitors and the like, can be delivered into the cells of a patient's body with relative ease and have been studied extensively. Targeting one specific factor in the viral infectious cycle, such agents have proven relatively ineffective against HIV. This is primarily due to the fact that strains of HIV change rapidly and become resistant to agents having a singular locus of effect (Richman, *AIDS Res. and Hum. Retrovir.*, 8, 1065–1071 (1992)). Accordingly, the problems of genetic variation and rapid mutation in HIV genomes compel consideration of new antiviral strategies to treat HIV infections. Along these lines, genetic antiviral agents are attractive, since they work at many different levels intracellularly.

Genetic antiviral agents differ from other therapeutic agents in that they are transferred as molecular elements into a target cell, wherein they protect the cell from viral infection (Baltimore, *Nature*, 325, 395–396 (1988); and Dropulic' et al., *Hum. Gene Ther.*, 5, 927–939 (1994)). Genetic antiviral agents can be any genetic sequence and include, but are not limited to, antisense molecules, RNA decoys, trans-dominant mutants, interferons, toxins, immunogens, and ribozymes. In particular, ribozymes are genetic antiviral agents that cleave target RNAs, including HIV RNA, in a sequence-specific fashion. The specificity of ribozyme-mediated cleavage of target RNA suggests the possible use of ribozymes as therapeutic inhibitors of viral replication, including HIV replication. Different types of ribozymes, such as the hammerhead and hairpin ribozymes, have been used in anti-HIV strategies (see, e.g., U.S. Pat. Nos. 5,144,019, 5,180,818 and 5,272,262, and PCT patent application nos. WO 94/01549 and WO 93/23569). Both of the hammerhead and hairpin ribozymes can be engineered to cleave any target RNA that contains a GUC sequence (Haseloff et al., *Nature*, 334, 585–591 (1988); Uhlenbeck, *Nature*, 334, 585 (1987); Hampel et al., *Nuc. Acids Res.*, 18, 299–304 (1990); and Symons, *Ann. Rev. Biochem.*, 61, 641–671 (1992)). Generally speaking, hammerhead ribozymes have two types of functional domains, a conserved catalytic domain flanked by two hybridization domains. The hybridization domains bind to sequences surrounding the GUC sequence and the catalytic domain cleaves the RNA target 3' to the GUC sequence (Uhlenbeck (1987), supra; Haseloff et al. (1988), supra; and Symons (1992), supra).

A number of studies have confirmed that ribozymes can be at least partially effective at inhibiting the propagation of HIV in tissue culture cells (see, e.g., Sarver et al., *Science*, 247, 1222–1225 (1990); Sarver et al., *NIH Res.*, 5, 63–67 (1993a); Dropulic' et al., *J. Virol.*, 66, 1432–1441 (1992); Dropulic' et al., *Methods: Comp. Meth. Enzymol.*, 5, 43–49 (1993); Ojwang et al., *PNAS*, 89, 10802–10806 (1992); Yu et al., *PNAS*, 90, 6340–6344 (1993); and Weerasinghe et al., *J. Virol.*, 65, 5531–5534 (1991)). In particular, Sarver et al. ((1990), supra) have demonstrated that hammerhead ribozymes designed to cleave within the transcribed region of the HIV gag gene, i.e., anti-gag ribozymes, could specifically cleave HIV gag RNAs in vitro. Furthermore, when cell lines expressing anti-gag ribozymes were challenged with HIV-1, a 50- to 100-fold inhibition of HIV replication was observed. Similarly, Weerasinghe et al. ((1991), supra) have shown that retroviral vectors encoding ribozymes designed to cleave within the U5 sequence of HIV-1 RNA confer HIV resistance to transduced cells upon subsequent challenge with HIV. Although different clones of transduced cells demonstrated different levels of resistance to challenge as determined by the promoter system used to drive ribozyme expression, most of the ribozyme-expressing cell lines succumbed to HIV expression after a limited time in culture.

Transduction of tissue culture cells with a provirus into the nef gene (which is not essential for viral replication in tissue culture) of which was introduced a ribozyme, the hybridization domains of which were specific for the U5 region of HIV, has been shown to inhibit viral replication within the transduced cells 100-fold as compared to cells transduced with wild-type proviruses (see, e.g., Dropulic' et al. (1992) and (1993), supra). Similarly, hairpin ribozymes have been shown to inhibit HIV replication in T-cells transduced with vectors containing U5 hairpin ribozymes and challenged with HIV (Ojwang et al. (1992), supra). Other studies have shown that vectors containing ribozymes expressed from a tRNA promoter also inhibit a variety of HIV strains (Yu et al. (1993), supra).

Delivery of ribozymes or other genetic antiviral agents to the cellular targets of HIV infection (e.g., CD4+ T-cells and monocytic macrophages) has been a major hurdle for effective genetic therapeutic treatment of AIDS. Current approaches for targeting cells of the hematopoietic system (i.e., the primary targets for HIV infection) call for introduction of therapeutic genes into precursor multipotent stem cells, which, upon differentiation, give rise to mature T-cells, or, alternatively, into the mature CD4+ T lymphocytes, themselves. The targeting of stem cells is problematic, however, since the cells are difficult to culture and transduce in vitro. The targeting of circulating T lymphocytes is also problematic, since these cells are so widely disseminated that it is difficult to reach all target cells using current vector delivery systems. Moreover, macrophages need to be considered as a cellular target, since they are the major reservoir for viral spread to other organs. However, since macrophages are terminally differentiated and, therefore, do not undergo cellular division, they are not readily transduced with commonly used vectors.

Accordingly, the predominant current approach to HIV treatment makes use of replication-defective viral vectors and packaging (i.e., "helper") cell lines (5ee, e.g., Buchschacher, *JAMA*, 269(22), 2880–2886 (1993); Anderson, *Science*, 256, 808–813 (1992); Miller, *Nature*, 357, 455–460 (1992); Mulligan, *Science*, 260, 926–931 (1993); Friedmann, *Science*, 244, 1275–1281 (1989); and Cournoyer et al., *Ann. Rev. Immunol.*, 11, 297–329 (1993)) to introduce into cells susceptible to viral infection (such as HIV infection) a foreign gene that specifically interferes with viral replication, or that causes the death of an infected cell (reviewed by Buchschacher (1993), supra). Such replication-defective viral vectors contain, in addition to the foreign gene of interest, the cis-acting sequences necessary for viral replication but not sequences that encode essential viral proteins. Consequently, such a vector is unable to complete the viral replicative cycle, and a helper cell line, which contains and constitutively expresses viral genes within its genome, is employed to propagate it. Following introduction of a replication-defective viral vector into a helper cell line, proteins required for viral particle formation are provided to the vector in trans, and vector viral particles capable of infecting target cells and expressing therein the gene, which interferes with viral replication or causes a virally infected cell to die, are produced.

Such replication-defective retroviral vectors include adenoviruses and adeno-associated viruses, as well as those retroviral vectors employed in clinical trials of HIV gene therapy, and, in particular, the mouse amphotropic retroviral vector known as the Moloney murine leukemia virus (MuLV). These defective viral vectors have been used to transduce CD4+ cells with genetic antiviral agents, such as anti-HIV ribozymes, with varying degrees of success (Sarver et al. (1990), supra; Weerasinghe et al. (1991), supra; Dropulic' et al. (1993), supra; Ojwang et al. (1992), supra; and Yu et al. (1993), supra). However, these vectors are intrinsically limited for HIV gene therapy applications. For example, a high transduction frequency is especially important in the treatment of HIV, where the vector has to transduce either rare CD34+ progenitor hematopoietic stem cells or widely disseminated target CD4+ T-cells, most of which, during the clinical "latent" stage of disease, are already infected with HIV. MuLV vectors, however, are difficult to obtain in high titer and, therefore, result in poor transduction. Furthermore, long-term expression of transduced DNA has not been obtained in CD34+ progenitor stem cells, in particular after differentiation to mature T lymphocytes. In addition, the use of defective viral vectors requires ex vivo gene transfer strategies (see, e.g., U.S. Pat. No. 5,399,346), which can be expensive and beyond the cost of the general population.

These shortcomings associated with the use of currently available vectors for genetic therapeutic treatment of AIDS have led researchers to seek out new viral vectors. One-such vector is HIV, itself. HIV vectors have been employed for infectivity studies (Page et al., *J. Virol.*, 64, 5270–5276 (1990)) and for the introduction of genes (such as suicide genes) into CD4+ cells, particularly CD4+ HIV-infected cells (see, e.g., Buchschacher et al., *Hum. Gener. Ther.*, 3, 391–397 (1992); Richardson et al., *J. Virol.*, 67, 3997–4005 (1993); Carroll et al., *J. Virol*, 68, 6047–6051 (1994); and Parolin et al., *J. Virol.*, 68, 3888–3895 (1994)). The strategy of these studies is to use HIV vectors to introduce genes into the CD4+ T-cells and monocytic cells.

To date, however, these vectors are extremely complex. Moreover, use of these vectors is accompanied by a risk of generating wild-type HIV via intracellular recombination. Cotransfection/coinfection of defective vector sequences and helper virus has been observed to result in recombination between homologous regions of the viral genomes (Inoue et al., *PNAS*, 88, 2278–282 (1991)). Observed complementation in vitro indicates that a similar replication-defective HIV vector could recombine in vivo, thus exacerbating an already existing HIV infection. The fact that retroviruses package two RNA genomes into one virion has led researchers to suggest that retroviruses carry two viral RNAs to circumvent any genetic defects caused by complementation and/or recombination (Inoue et al. (1991), supra).

In addition to the risk of intracellular recombination, thereby resulting in wild-type HIV, HIV vectors have an associated risk of mutation in vivo, which increases the pathogenicity of the viral vector. This has lead Sarver et al. (*AIDS Res. and Hum. Retrovir.*, 9, 483–487 (1993b)) to speculate regarding the development of second-generation recombinant HIV vectors, which are replication-competent, yet nonpathogenic. Such vectors, in comparison with the predominantly used nonreplicating vectors (i.e., replication-deficient vectors) continue to replicate in a patient, thus providing constant competition with wild-type HIV. So far, however, such vectors are not available.

Ideally, the best opportunity to treat an infected individual occurs at the time of inoculation, before the virus even infects the host. However, this is difficult to accomplish inasmuch as many individuals do not realize they have become infected with HIV until the clinical latent phase of disease. Based on this, the stage at which antiviral intervention is most sorely needed is during clinical latency. Therapy at this stage requires that the challenge presented by the large number of already infected CD4+ lymphocytes, which harbor viral genomes, be confronted. This is no trivial challenge, as evidenced by the fact that, to date, HIV remains incurable and is only poorly treatable by currently available therapies. An effective vaccine is not forthcoming, and, although inhibitors of reverse transcriptase and protease have been shown to prevent HIV replication in tissue culture, the development of viral resistance in vivo has led to treatment failure. Thus, HIV gene therapy may have little benefit for the vast majority of HIV-infected individuals, predicted to reach more than 40 million by the year 2000.

In view of the above, it is also becoming increasingly important to develop long-term and persistent immunological responses to certain pathogens, especially viruses, particularly in the context of AIDS and cancer, for example. Live-attenuated (LA) vaccines, using replication-competent, but nonpathogenic viruses have been considered (Daniel et al., *Science*, 258, 1938–1941 (1992); and Desrosiers, *AIDS Res. & Human Retrovir.*, 10, 331–332 (1994)). However, such nonpathogenic viruses, which differ from the rcrre-spo?j.dilig wild-type viruses by a deletion in one or more genes, either (i) cannot elicit a protective immune response because the antigen does not persist (because the LA-virus does not efficiently replicate); or (ii) the LA-virus replicates but has other pathogenic potential, as witnessed by the ability of the LA-virus to cause disease in young animal models (Baba et al., *Science*, 267, 1823–1825 (1995)).

For the aforementioned reasons, there remains a need for alternative prophylactic and therapeutic treatment modalities of viral infection, particularly in the context of AIDS and cancer. The present invention provides such alternative methods by providing a conditionally replicating vector. The invention also provides additional methods in which such a vector can be employed. These and other objects and advantages of the present invention, as well as additional inventive features, will be apparent from the description of the invention set forth herein.

BRIEF SUMMARY OF THE INVENTION

The present invention provides a conditionally replicating viral vector, which is characterized by a capacity to replicate only in a host cell that is permissive for replication of the vector.

In one embodiment, the conditionally replicating viral vector comprises at least one nucleic acid sequence, the presence, transcription or translation of which confers to the vector in a replication-permissive host cell a selective advantage over a wild-type strain of virus corresponding to the virus from which the vector was derived.

In another embodiment of the conditionally replicating viral vector, the vector, which preferably is a retrovirus, comprises at least one nucleic acid sequence, the presence, transcription or translation of which confers to a host cell, which is infected with the vector, a selective advantage over a cell infected with a wild-type strain of virus corresponding to the virus from which the vector was derived.

Also provided by the present invention is a pharmaceutical composition comprising a conditionally replicating viral vector and a pharmaceutically acceptable carrier. Further provided is a host cell comprising a conditionally replicating viral vector. A vector, wherein said vector, if DNA, comprises a nucleotide sequence selected from the group consisting of SEQ ID NOS: 2, 4, 5, 6, 7, 15, 16, 17 and 18 and wherein said vector, if RNA, comprises a nucleotide sequence encoded by a nucleotide sequence selected from the group consisting of SEQ ID NOS: 2, 4, 5, 6, 7, 15, 16, 17 and 18 is also provided as are isolated and purified nucleic acid molecules as set forth herein. Similarly provided are a method of engendering a vector with a ribozyme, a method of modifying a vector, and a method of propagating and selectively packaging a conditionally replicating vector without using a packaging cell line.

In yet another embodiment of the present invention, a method of therapeutically and prophylactically treating a host cell for a viral infection is provided. Such methods can additionally comprise the use of a helper-expression vector, a cytotoxic drug, proteins/factors, or a protease/reverse transcriptase inhibitor as appropriate. The method can be used, for example, to inhibit replication of a virus, treat cancer, in vivo gene transfer, or to express a gene of interest in a host cell.

In still yet another embodiment, a method of using a host cell comprising a conditionally replicating vector to detect interaction between a drug/factor and a protein is provided. Such a method enables protein characterization and screening of drugs/factors for activity with respect to a given protein.

BRIEF DESCRIPTION OF THE FIGURES

FIGS. 1A–1E are schematic depictions of the structure of the viral genome present in wild-type HIV (FIG. 1A), crHIV-1.1 (FIG. 1B), crHIV-1.11 (FIG. 1C), crHIV-1.12 (FIG. 1D), and crHIV-1.111 (FIG. 1E). Designations: cr, conditionally replicating; U5, U5 coding sequence; Rz, ribozyme; Ψ, packaging signal; gag, pol and env, the coding sequence for proteins that form the viral core, reverse transcriptase, and envelope, respectively; tat, rev, rre, and nef, additional viral genes; open boxes, viral long-terminal repeats. The crosses in the wild-type U5 coding region indicate the approximate regions in which ribozymes according to the invention cleave in the wild-type U5 RNA, but not modified crHIV U5 RNA (i.e., "mU5").

FIG. 2 depicts the DNA sequences of wild-type HIV U5 RNA [SEQ ID NO:1] (A) and modified crHIV U5 RNA [SEQ ID NO:2] (B). Numbers refer to the number of bases downstream from the start of transcription.

FIG. 10A: Production of virions that contain crHIV-1.111 RNA in stimulated ACH2 cells transfected with crHIV-1.111 (lane 4) or with pGEM 3Z (lane 2). Lanes 1 and 3 comprise RT-PCR negative controls. FIG. 10B: Production of crHIV-1.11 ribozyme DNA after infection of Jurkat cells with the supernatants of stimulated ACH2 cells that previously were (lane 2) or were not (lane 1) transfected with crHIV-1.11. FIG. 10C: Production of virions that contain crHIV-1.11 RNA in Jurkat cells that were first transfected with crHIV-1.11, and were then superinfected with pNL4-3 virus (lane 2). Also shown is virion production in cells that were first transfected with pGEM 3Z control plasmid and then superinfected with pNL4-3 virus (lane 2). Lanes 1 and 3 comprise RT-PCR negative controls.

FIG. 12 is an autoradiograph depicting primer extension using the PE primer of virion-associated RNAs from crHIV-1.11 cultures at the late stages of viral growth in cells transfected with wild-type HIV alone (lane 1), or co-transfected with both wild-type HIV and crHIV-1.11 (lane 2).

DESCRIPTION OF THE PREFERRED EMBODIMENTS

Figure 1A:
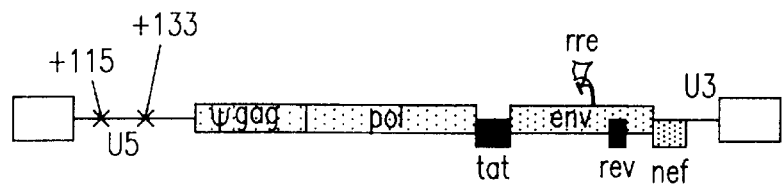

The present invention provides a method of inhibiting the replication of a wild-type strain of a virus. The method comprises contacting a host, which is capable of being infected with such a wild-type strain of virus, and preferably is actually infected with such a wild-type strain of virus, with a vector that is propagated only in a host that is permissive for the replication of the vector (i.e., a nonpathogenic, conditionally replicating (cr) vector).

As further described herein, a particular aim of the method is to establish a competitive infection in the host with such a nonpathogenic, conditionally replicating vector. Generally, a conditionally-replicating vector according to the invention comprises at least one nucleic acid sequence that confers a selective advantage for replication and spread to the conditionally replicating vector as compared with a wild-type virus, and/or at least one nucleic acid sequence that confers a selective advantage for propagation of viral particles to a host cell containing a conditionally replicating vector as compared with a host cell containing a wild-type virus.

In a preferred embodiment of the invention, the vector comprises an HIV sequence and is employed for treatment of HIV infection. Thus, the vector, or a host cell containing the vector, comprises at least one nucleic acid sequence that (1) provides a crHIV genome with a selective advantage over a wild-type HIV genome for packaging into progeny virions (i.e., in cells where they both reside), and/or (2) provides a host cell producing a conditionally replicating vector (virus) with a selective advantage for production of a crHIV virion, as compared with a host cell producing a wild-type virus. One method (to which the invention is not limited) is to confer crHIV genomes with a selective advantage for packaging by providing them with one or more ribozymes capable of cleaving the wild-type HIV genome.

Wild-Type Virus

According to the invention, a "virus" is an infectious agent that consists of protein and nucleic acid, and that uses a host cell's genetic machinery to produce viral products specified by the viral nucleic acid. A "nucleic acid" refers to a polymer of DNA or RNA that is single or double-stranded, linear or circular, and, optionally, contains synthetic, nonnatural, or modified nucleotides, which are capable of being incorporated into DNA or RNA polymers. A DNA polynucleotide preferably is comprised of genomic or cDNA sequences.

A "wild-type strain of a virus" is a strain that does not comprise any of the human-made mutations as described herein, i.e., any virus that can be isolated from nature. Alternatively, a wild-type strain is any virus that has been cultured in a laboratory, but still, in the absence of any other virus, is capable of producing progeny genomes or virions like those isolated from nature. For example, the pNL4-3 HIV molecular clone described in the following Examples is a wild-type strain.

In general, the method of the present invention preferably is employed to treat viral diseases that result from viral infection. Desirably, a virus (as well as the vector, as discussed below) is a RNA virus, but also can be a DNA virus. RNA viruses are a diverse group that infects prokaryotes (e.g., the bacteriophages) as well as many eukaryotes, including mammals and, particularly, humans. Most RNA viruses have single-stranded RNA as their genetic material, although at least one family has double-stranded RNA as the genetic material. The RNA viruses are divided into three main groups: the positive-stranded viruses (i.e., those of which the genome transferred by the virus is translated into protein, and whose deproteinized nucleic acid is sufficient to initiate infection), the negative-stranded viruses (i.e., those of which the genome transferred by the virus is complementary to the message sense, and must be transcribed by virion-associated enzymes before translation can occur), and the double-stranded RNA viruses. The method of the present invention preferably is employed to treat positive-stranded viruses, negative-stranded viruses, and double-stranded RNA viruses.

As employed herein, a RNA virus encompasses Sindbis-like viruses (e.g., Togaviridae, Bromovirus, Cucumovirus, Tobamovirus, Ilarvirus, Tobravirus, and Potexvirus), Picornavirus-like viruses (e.g., Picornaviridae, Caliciviridae, Comovirus, Nepovirus, and Potyvirus), minus-stranded viruses (e.g., Paramyxoviridae, Rhabdoviridae, Orthomyxoviridae, Bunyaviridae, and Arenaviridae), double-stranded viruses (e.g., Reoviridae and Birnaviridae), Flavivirus-like viruses (e.g., Flaviviridae and Pestivirus), Retrovirus-like viruses (e.g., Retroviridae), Coronaviridae, and other viral groups including, but not limited to, Nodaviridae.

A preferred RNA virus according to the invention is a virus of the family Flaviviridae, preferably a virus of the genus Filovirus, and especially a Marburg or Ebola virus. Preferably, a virus of the family Flaviviridae is a virus of the genus Flavivirus, such as yellow fever virus, dengue virus, West Nile virus, St. Louis encephalitis virus, Japanese encephalitis virus, Murray Valley encephalitis virus, Rocio virus, tick-borne encephalitis virus, and the like.

Also preferred is a virus of the family Picornaviridae, preferably a hepatitis A virus (HAV), hepatitis B virus (HBV), or a non-A or non-B hepatitis virus.

Another preferred RNA virus is a virus of the family Retroviridae (i.e., a retrovirus), particularly a virus of the genus or subfamily Oncovirinae, Spumavirinae, Spumavirus, Lentivirinae, and Lentivirus. A RNA virus of the subfamily Oncovirinae is desirably a human T-lymphotropic virus type 1 or 2 (i.e., HTLV-1 or HTLV-2) or bovine leukemia virus (BLV), an avian leukosis-sarcoma virus (e.g., Rous sarcoma virus (RSV), avian myeloblastosis virus (AMV), avian erythroblastosis virus (AEV), and Rous-associated virus (RAV; RAV-0 to RAV-50), a mammalian C-type virus (e.g., Moloney murine leukemia virus (MuLV), Harvey murine sarcoma virus (HaMSV), Abelson murine leukemia virus (A-MuLV), AKR-MuLV, feline leukemia virus (FeLV), simian sarcoma virus, reticuloendotheliosis virus (REV), spleen necrosis virus (SNV)), a B-type virus (e.g., mouse mammary tumor virus (MMTV)), and a D-type virus (e.g., Mason-Pfizer monkey virus (MPMV) and "SAIDS" viruses). A RNA virus of the subfamily Lentivirus is desirably a human immunodeficiency virus type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. The acronym "HIV" or terms "AIDS virus" or "human immunodeficiency virus" are used herein to refer to these HIV viruses, and HIV-related and associated viruses, generically. Moreover, a RNA virus of the subfamily Lentivirus preferably is a Visna/maedi virus (e.g., such as infect sheep), a feline immunodeficiency virus (FIV), bovine lentivirus, simian immunodeficiency virus (SIV), an equine infectious anemia virus (EIAV), and a caprine arthritis-encephalitis virus (CAEV).

A virus according to the invention also desirably is a DNA virus. Preferably, the DNA virus is an Epstein-Barr virus, an adenovirus, a herpes simplex virus, a papilloma virus, a vaccinia virus, and the like.

Many of these viruses are classified as "Biosafety Level 4" (i.e., World Health Organization (WHO) "Risk Group 4") pathogens for which maximum containment facilities are required for all laboratory work. The ordinary skilled artisan, however, is familiar with and is capable of adhering to the safety precautions necessary for these viruses.

A "host cell" can be any cell, and, preferably, is a eukaryotic cell. Desirably, the host cell is a lymphocyte (such as a T lymphocyte) or a macrophage (such as a monocytic macrophage), or is a precursor to either of these cells, such as a hematopoietic stem cell. Preferably, the cells comprise a CD4+ glycoprotein on the cell surface, i.e., are CD4+. Desirably, however, a CD4+ T lymphocyte, which has been infected with the AIDS virus, has not yet become activated (i.e., preferably expression of nef has not yet occurred, and, even more preferably, CD4 gene expression has not been downregulated, as further discussed below). Moreover, a host cell preferably is a cell that lacks the CD4 marker, and yet is capable of being infected by a virus according to the present invention. Such a cell includes, but is not limited to, an astrocyte, a skin fibroblast, a bowel epithelial cell, and the like. Preferably, the host cell is of a eukaryotic, multicellular species (e.g. as opposed to a unicellular yeast cell), and, even more preferably, is a mammalian, e.g., human, cell. A cell can be present as a single entity, or can be part of a larger collection of cells. Such a "larger collection of cells" can comprise, for instance, a cell culture (either mixed or pure), a tissue (e.g., epithelial or other tissue), an organ (e.g., heart, lung, liver, gallbladder, urinary bladder, eye, and other organs), an organ system (e.g., circulatory system, respiratory system, gastrointestinal system, urinary system, nervous system, integumentary system or other organ system), or an organism (e.g., a bird, mammal, or the like). Preferably, the organs/tissues/cells being targeted are of the circulatory system (e.g., including, but not limited to heart, blood vessels, and blood), respiratory system (e.g., nose, pharynx, larynx, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to, brain and spinal cord, and special sense organs, such as the eye) and integumentary system (e.g., skin). Even more preferably, the cells being targeted are selected from the group consisting of heart, blood vessel, lung, liver, gallbladder, urinary bladder, and eye cells.

Vector

A "vector" is a nucleic acid molecule (typically DNA or RNA) that serves to transfer a passenger nucleic acid sequence (i.e., DNA or RNA) into a host cell. Three common types of vectors include plasmids, phages and viruses. Preferably, the vector is a virus.

Desirably, the vector is not a wild-type strain of a virus, inasmuch as it comprises human-made mutations. Thus, the vector typically is derived from a wild-type viral strain by genetic manipulation (i.e., by deletion) to comprise a conditionally replicating virus, as further described herein. Optimally, the viral vector comprises a strain of virus that is of the same type as the wild-type virus causing the infection being treated, which, preferably, is one of the aforementioned wild-type viruses. Accordingly, preferably, the vector is derived from a RNA virus, even more preferably, the vector is derived from a retrovirus, and, optimally, the vector is derived from a human immunodeficiency virus. Such a vector derived from a human immunodeficiency virus is referred to generically herein as a "crHIV" vector.

A vector also, preferably, is a "chimeric vector," e.g., a combination of a viral vector with other sequences, such as, for instance, a combination of HIV sequences with another virus (which, desirably, is derived from a wild-type viral strain to comprise a conditionally replicating vector). In particular, HIV sequences desirably can be linked with sequences of a modified (i.e., non-wild-type) strain of adenovirus, adeno-associated virus, a Sindbis virus vector, or an amphotropic murine retroviral vector.

As encompassed herein, a vector can comprise either DNA or RNA. For instance, either a DNA or RNA vector can be used to derive the virus. Similarly, a cDNA copy can be made of a viral RNA genome. Alternatively, a cDNA (or viral genomic DNA) moiety can be transcribed in vitro to produce RNA. These techniques are well-known to those skilled in the art, and also are described in the following Examples.

A "conditionally replicating virus" is a replication-defective virus, which is defective only under certain conditions. In particular, the virus can complete its replicative cycle in a permissive host cell, and cannot complete its replicative cycle in 4 restrictive host cell. A "permissive host cell" is a host cell infected with a wild-type strain of virus. Such infection can occur either before co after infection with a conditionally replicating virus according to the invention. Alternatively, a "permissive host cell" is one that encodes wild-type viral gene products necessary for viral replication. Thus, a conditionally replicating vector according to the invention is a virus (which preferably is the same type of virus as the infection being treated) that replicates only upon complementation with a wild-type strain of virus or when wild-type virus infects cells containing conditionally replicating vector genomes.

In a preferred embodiment, a vector comprises an RNA virus (e.g., a conditionally replicating HIV virus), which is introduced in the form of DNA. This preferred embodiment provides a replicating HIV-1 (crHIV) vector strategy that affords nonpathogenic crHIV-l vector genomes with a selective advantage over pathogenic wild-type HIV genomes. Specifically, in cells containing both wild-type HIV and crHIV genomes, crHIV RNAs have a selective advantage for packaging into virions because they-contain, for instance, ribozymes that cleave wild-type RNA, but not crHIV RNA. Such nonpathogenic crHIVs are able to spread to uninfected cells that are susceptible to HIV infection (e.g., CD4+ cells) in the presence of wild-type helper virus. In this manner, selective packaging and spread of crHIV interferes with wild-type HIV replication.

In particular, crHIV genomes are introduced into infected cells or uninfected cells. Infected cells supply the crHIV genome with proteins required for encapsidation and production of progeny virions. crHIV genomes are introduced into uninfected cells preferably either directly by transduction (e.g., this can be done, for instance, by liposome-mediated transduction of crHIV DNA, or by using a chimeric viral vector), or by infection of crHIV particles that result from transfection or wild-type HIV-infected cells. Uninfected cells on their own do not produce crHIV particles. However, they can become superinfected with wild-type virus, which supplies the proteins required for the further production of crHIV particles. In this sense, a conditionally replicating vector according to the invention also functions as a type of "viral delivery vector" that provides the means by which multiple rounds of crHIV infection (i.e., in the presence of concurrent infection with wild-type HIV) can ensue. Such a vector, which provides a source of virus for more than one round of viral replication, contrasts with other currently employed vectors, such as those used with packaging cell lines, and which provide for only a single round of replication.

If desired (e.g., to facilitate use of the vector in vitro), wild-type viral gene products can be co-supplied to a cell infected with the conditionally replicating vector. Wild-type viral gene products can be supplied not only by co-infection with a wild-type viral strain (or a cDNA or provirus of a RNA virus), but also by supplying them to a cell in the form of their genes subcloned in an expression vector, e.g., a helper expression vector ("helper"), that is capable of imparting on a host cell transcription or translation of the sequences (regulatory or structural), or, alternatively, the gene products can be supplied exogenously, i.e., by adding the protein products to the cell. With respect to the "helper," its expression can be cell specific or not cell-specific and it can be introduced into a host cell in concert with a conditionally replicating viral vector as defined herein and, thereby, enable continuous replication of the conditionally replicating viral vector.

As used herein, "complementation" refers to the nongenetic interaction of viral gene products from different sources in cells. Specifically, with a mixed infection, complementation comprises an enhancement En the viral yield of one or both parental genomes, while the genotypes of the parental genomes remain unchanged. Complementation can be nonallelic (i.e., intergenic, wherein mutants defective in different functions assist each other in viral replication by supplying the function that is defective in the other virus) or allellic (i.e., intragenic, wherein the two parents have defects in different domains of a multimeric protein).

Desirably, the types of cells that can be transfected (transduced) with crHIV DNA (i.e., by liposomes or by using an adenoviral vector or an amphotropic retroviral vector) can be either HIV-infected or uninfected cells. HIV infected cells can be activated or unactivated. If they are activated, they will immediately transcribe wild-type HIV RNA and crHIV RNA, resulting in selective packaging of crHIV RNA into progeny virions. If HIV-infected cells are not activated, the crHIV DNA will reside in them until they become activated (e.g., through stimulation by mitogens, antigens, and the like), resulting again in selective packaging of crHIV RNA into progeny virions. Both activated and unactivated uninfected cells that are transfected with crHIV DNA will not produce virions until they become superinfected with wild-type HIV and activated by stimulation, resulting again in selective packaging of crHIV RNA into progeny virions.

Superinfection of cells containing crHIV genomes (e.g., as a result of transfection or infection) occurs because crHIV genomes do not encode viral proteins that block superinfection (such as env and nef). The resulting crHIV virions can infect uninfected cells because the viral particles contain the reverse transcriptase molecule, which all HIV particles carry so that they can create a DNA provirus from their genomic RNA. This process is called reverse transcription. Once crHIV virions infect uninfected cells, they can undergo reverse transcription and produce a provirus from their genomic RNA. Thus, these cells are the equivalent to those uninfected cells that are directly transduced with crHIV DNA. They cannot produce crHIV particles until these cells become superinfected with wild-type HIV and become activated, then once again, selective packaging of crHIV RNA into progeny virions occurs. It is possible that crHIV particles could also infect some cells that are already infected with HIV (see, e.g., Yunoki et al., *Arch. Virol.,* 116, 143–158 (1991); Winslow et al., *Virol.,* 196, 849–854 (1993); Chen et al., *Nuc. Acids Res.,* 20, 4581–4589 (1992); and Kim et al., *AIDS Res. & Hum. Retrovir.,* 9, 875–882 (1993)). However, for this to occur, these HIV-infected cells must not express proteins that down-regulate CD4 expression, because this will prevent the crHIV virions from infecting these cells. Activated, HIV-infected cells generally down-regulate CD4 expression. Accordingly, HIV-infected cells that are not activated are potentially susceptible to crHIV superinfection and, thus, could be another source for crHIV particle production.

With a preferred crHIV vector according to the invention, the vector comprises sequences required for RNA transcription, tRNA primer binding, dimerization and packaging, and either lacks sequences encoding proteins that block superinfection with wild-type HIV (e.g., nef or env proteins) or comprises such sequences but they are either not transcribed or not translated into functional protein, such that their expression is deemed "silent." Even more preferably, the vector lacks the region or sequences coding the region of wild-type HIV from within the gag coding sequence to and including the nef gene. optimally, however, the vector does comprise the rev responsive element (RRE), which is cloned into the vector in the region of the deletion or some other convenient region. Such a preferred HIV vector is said to "lack the region or sequences coding the region" inasmuch as this vector can be administered in its RNA manifestation, or, alternatively, as DNA, as previously described.

Vector construction is well-known to those skilled in the art. For instance, and as described in Example 1, the DNA manifestation of a RNA virus, such as HIV, is cleaved using restriction enzymes to excise HIV encoding sequences from within the gag coding region to within the U3 region, following the nef gene. A cloning cassette comprised of a polylinker containing multiple restriction sites is inserted into the region of the deletion prior to ligation to provide convenient restriction sites for cloning into the vector. A DNA fragment containing RRE is subcloned into one of these sites. The resultant vector produces a truncated gag transcript, and does not produce wild-type Gag protein, or any other wild-type HIV proteins. Moreover, it is not necessary that the vector express even the truncated gag protein inasmuch as the gag translation initiation sequence can be mutated to prevent its translation.

Using the same approach, the crHIV sequences can be linked to other sequences, such as those of a virus or other vector, to derive a chimeric vector. For instance, the crHIV sequences can be ligated to those of Sindbis virus, AAV, adenovirus, or amphotropic retrovirus to name but a few such viruses that can be used to provide for delivery of the crHIV sequences. With such a chimeric vector, the vector can be introduced into the cell either using the conjoined virus's mechanism for cell entry (e.g., receptor-mediated endocytosis for adenovirus) or other means, e.g., liposomes.

Preferably, according to the invention, a vector (i.e., a conditionally replicating virus that preferably is a crHIV vector) comprises at least one nucleic acid sequence, the possession (i.e., presence, transcription or translation) of which confers a selective advantage. There are two types of such nucleic acid sequences contemplated for inclusion in the vector: (1) a nucleic acid sequence, the possession of which optimally confers a selective advantage for viral replication and spread to a vector comprising such a sequence over a wild-type strain of virus (i.e., preferably, a wild-type strain from which the vector was derived, and which does not comprise the sequence), and (2) a nucleic acid sequence, the possession of which optimally confers a selective advantage to cells infected with a vector comprising the sequence as compared with cells infected with a wild-type strain of virus (i.e., preferably, a wild-type strain from which the vector was derived (and also, for example, a helper-expression vector that promotes vector replication and/or function in an uninfected host cell), and which does not comprise the sequence) by, for example, promoting cell survival, promoting vector particle production and/or propagation, promoting the production of crHIV vector virions from crHIV vector-producing cells, inducing apoptosis, facilitating protein production or promoting immunological function or targeting, so as to achieve a desired prophylactic, therapeutic or biological outcome. Each of these sequences, or a plurality of each of these sequences, i.e., a sequence that alone or in combination with another factor(s), promotes the propagation of the vector and/or promotes a particular host cell function so as to enable a favorable prophylactic, therapeutic and/or biological outcome, can be included in the vector, either in the absence or the presence of the other sequence, i.e., the vector can comprise "at least one nucleic acid sequence" and "at least one additional nucleic acid sequence."

A "nucleic acid" is as previously described. A "nucleic acid sequence" in particular comprises any gene or coding sequence (i.e., DNA or RNA) of potentially any size (i.e., limited, of course, by any packaging constraints imposed by the vector), the possession of which confers a selective advantage, as further defined herein. A "gene" is any nucleic acid sequence coding for a protein or a nascent MRNA molecule (regardless of whether the sequence is transcribed and/or translated). Whereas a gene comprises coding sequences as well as noncoding sequences (e.g., regulatory sequences), a "coding sequence" does not include any noncoding DNA.

1. Nucleic acid sequence, the possession of which confers a selective advantage in a host cell to a vector comprising such a sequence over a wild-type strain of virus.

A nucleic acid sequence, which confers a selective advantage to a vector in a host cell over a wild-type strain of virus, preferably is any sequence that allows viral particles propagated from the vector to be selectively produced or packaged as compared with viral particles propagated from the wild-type virus. Such sequences include, but are not limited to, a sequence that results in an increase in the number of vector genomes produced intracellularly as compared with wild-type genomes, and an antiviral nucleic acid sequence.

The first category of nucleic acid sequences that confer a selective advantage in a host cell to a vector containing the sequence as compared with a wild-type strain of virus are sequences such as a promoter. A "promoter" is a sequence that directs the binding of RNA polymerase and thereby promotes RNA synthesis, and that can comprise one or more enhancers. "Enhancers" are cis-acting elements that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

Accordingly, preferably, the promoter (e.g., the long-terminal repeat (LTR)) of a conditionally replicating HIV vector is modified such that the vector is more responsive to certain cytokines than is the wild-type HIV strain. For instance, a modified HIV promoter is available that demonstrates increased transcriptional activity in the presence of interleukin-2. Incorporation of this promoter into a vector and introduction of the vector into wild-type, HIV-infected cells preferably results in increased production and packaging of progeny virions from the vector genome as compared with the wild-type HIV genome. Other cytokines and/or chemokines (e.g., including, but not limited to, tumor necrosis factor $\alpha$, RANTES, and the like) similarly can be employed to promote selective packaging of virions encoded by the vector.

The second category of a nucleic acid sequence that confers a selective advantage to a vector containing the sequence as compared with a wild-type strain of virus includes, as a preferred nucleic acid sequence, an antiviral nucleic acid sequence. "Antiviral agents" are categorized by their mode of action, e.g., inhibitors of reverse transcriptase, competitors for viral entry into cells, vaccines, protease inhibitors, and genetic antivirals. "Genetic antiviral agents" are DNA or RNA molecules that are transferred into cells and affect their intracellular targets either directly (i.e., as introduced intracellularly) or after their conversion to either RNA or protein (reviewed by Dropulic et al. (1994), supra). A genetic antiviral sequence also is a preferred nucleic acid sequence. Genetic antiviral agents include, but are not limited to, antisense molecules, RNA decoys, transdominant mutants, toxins, immunogens, and ribozymes. Desirably, a genetic antiviral is an antisense molecule, an immunogen, and a ribozyme. Accordingly, a preferred nucleic acid sequence that confers a selective advantage to a vector over a wild-type strain of virus is that of a genetic antiviral agent selected from the group consisting of an antisense molecule, an immunogen, and a ribozyme.

An "antisense molecule" is a molecule that mirrors a short segment of a gene whose expression is to be blocked. An antisense molecule directed against HIV hybridizes to wild-type HIV RNA, allowing its preferential degradation by cellular nucleases. Antisense molecules preferably are DNA oligonucleotides, desirably of about 20 to about 200 base pairs in length, preferably about 20 to about 50 base pairs in length, and, optimally, less than 25 base pairs in length. An antisense molecule can be expressed from crHIV RNA that preferentially binds to genomic wild-type RNA, thereby providing the crHIV RNA with a selective advantage for packaging into progeny virions.

An "immunogen" is a single-chain antibody (scAb) directed to a viral structural protein. An immunogen is transferred as nucleic acid and expressed intracellularly. Similarly, an immunogen also can be any antigen, surface protein, (including those that are class-restricted) or antibody, which facilitates vector and/or host cell selection. In a preferred vector, the nucleic acid sequence comprises a scAb that binds to wild-type HIV Rev protein. This preferably prevents maturation of Rev protein by resulting in its withholding in the endoplasmic reticulum. Specifically, Rev proteins export unspliced HIV RNA to the cytoplasm by binding to the RRE and then oligomerizing to surround the HIV RNA. HIV RNAs that are complexed with Rev are exported into the cytoplasm and bypass the cell's splicing machinery. Thus, if wild-type Rev does not bind to the wild-type RRE, then wild-type HIV RNAs are not exported into the cytoplasm, and are not encapsidated into progeny virions.

Optimally, the vector containing the scAb nucleic acid sequence further comprises a modified RRE sequence, -an encodes a mutated Rev protein that recognizes the modified, but not the wild-type, RRE. Accordingly, in cells containing wild-type HIV and a vector comprising the scAb nucleic acid sequence, the vector preferentially is packaged into virions. A similar strategy preferably is employed wherein proteins of the wild-type HIV matrix or nucleocapsid (i.e., or any protein involved in protein/RNA interactions that affect encapsidation of viral RNA) are the targets of the scAb.

A "ribozyme" is an antisense molecule with catalytic activity, i.e., instead of binding RNA and inhibiting translation, ribozymes bind RNA and effect site-specific cleavage of the bound RNA molecule. Generally, there are four ribozyme groups: the Tetrahymena group I intervening sequence, RNase 2, and the hammerhead and hairpin ribozymes. However additional catalytic motifs also exist in other RNA molecules, e.g., hepatitis delta virus and ribosomal RNAs in fungal mitochondria.

A preferred ribozyme is a ribozyme in which the catalytic domain cleaves a 3'-nucleotide NUH sequence [SEQ ID NO:3], wherein N can be any nucleotide (i.e., G, A, U or C), and H can be either an A, C or U. However, inasmuch as the sequence that is cleaved most efficiently by such ribozymes is a GUC site, preferably the NUH sequence comprises a GUC site.

Desirably, such a ribozyme cleaves in a region of a wild-type strain of virus or its transcripts, but does not cleave in a region of a vector or its transcripts. The ribozyme cleaves the virus or its transcripts in the sense that such a virus or vector can be either RNA or DNA, as previously described. By cleavage "in a region" is meant cleavage in a targeted region, i.e., preferably a region of the virus that is necessary for viral propagation. Desirably, the vector has been modified so that this particular region being targeted (i.e., if present in the vector at all) is not cleaved by the ribozyme. Optionally, the ribozyme can cleave the vector so long as cleavage does not occur in a region required for propagation of viral, e.g., crHIV particles.

Optimally, the ribozyme is encoded by a sequence selected from the group consisting of SEQ ID NO:4 (i.e., CACACAACACTGATGAGGCCGAAAGGCCGAA ACGGGCACA) and SEQ ID NQ:5 (i.e., ATCTCTAGTC TGATGAGGCCGAAAGGCCGAAACCAGAGTC). Whereas SEQ ID NO:4 comprises a ribozyme that is targeted to the +115 site (i.e., in terms of the number of bases downstream from the start of transcription) of the wild-type HIV U5 region, SEQ ID NO:5 comprises a ribozyme that is targeted to the +133 site of the wild-type HIV U5 region.

Such a ribozyme is able to cleave within the wild-type HIV genome (or its transcripts) but not the vector genome (or its transcripts) inasmuch as the vector U5 sequences are modified by in vitro site-directed mutagenesis, such as is known in the art and described in Example 1. In particular, the vector sequences preferably are modified such that the vector comprises a sequence selected from the group consisting of SEQ ID NO:2 (i.e., GTGTGCCCACCTGTTGTGTGACTCTGGCAGCTAGA GAAC), SEQ ID NO:4, SEQ ID NO:5, SEQ ID NO:6 (i.e., GTGTGCCCGCCTGTTGTGTGACTCTGGTAACTAGA GATC), SEQ ID NO:7 (i.e., GTGTGCCCGTCTGTTGT GTGACTCTGGCAAC TAGAGATC), SEQ ID NO:15, SEQ ID NO:16, SEQ ID NO:17, and SEQ ID NO:18. In the form of RNA, the vector preferably comprises a sequence encoded by a sequence selected from the group consisting of SEQ ID NO:2, SEQ ID NO:4, SEQ ID NO:5, SEQ ID NO:6, SEQ ID NO:7, SEQ ID NO:15, SEQ ID NO:16, SEQ ID NO:17, and SEQ ID NO:18. In contrast, wild-type HIV comprises the U5 sequence encoded by the sequence of SEQ ID NO:1 (i.e., GTGTGCCCGTCTGTTGTGTGACTCTG GTAACTAGAGATC). The modifications in toto and comparison to the wild-type U5 sequence (in the form of DNA) are set out in FIG. 2.

Moreover, other ribozymes targeted to other regions of a viral and, particularly, a HIV genome can be employed, either alone or in combination. For instance, the ribozyme can cleave within other RNA sequences needed for viral replication, e.g., within the reverse transcriptase, protease, or transactivator protein, within Rev, or within other necessary sequences, such as have been described. Preferably, a vector comprises multiple ribozymes, e.g., targeted to multiple sites. In such cases, the analogous sequences in the vector are modified by site-directed mutagenesis, or some other means such as is known in the art, to derive a vector that is resistant to such ribozyme cleavage.

When the vector is a human immunodeficiency virus, preferably the vector lacks the tat gene and its 5' splice site and, in place thereof, comprises a triple anti-Tat ribozyme cassette, wherein the catalytic domain of each ribozyme of the triple ribozyme cassette cleaves a different site on a wild-type human immunodeficiency viral nucleic acid molecule, in particular a different site within tat. Preferably, the catalytic domain of each ribozyme cleaves a nucleotide sequence in a region of a nucleic acid molecule of wild-type human immunodeficiency virus for which there is no ribozyme-resistant counterpart in the vector, itself.

2. Nucleic acid sequence, the possession of which confers a selective advantage to cells infected with a vector comprising the sequence as compared with cells infected with a wild-type strain of virus.

A nucleic acid sequence that confers a selective advantage to a cell containing a vector comprising the sequence over a cell containing a wild-type strain of virus (i.e., that lacks the sequence) preferably is any sequence that allows a cell containing the vector to survive and propagate viral particles (i.e., crHIV viral particles) as compared with a cell containing the wild-type virus. Such sequences include, but are not limited to, any sequence that allows the cell, or the vector contained in the cell, to escape destruction, sequences that promote cell survival, sequences that induce apoptosis, sequences that facilitate protein production or sequences that promote immune function or targeting.

For instance, preferably such a nucleic acid sequence contained on the vector encodes genes for multidrug resistance (see., e.g., Ueda et al., *Biochem. Biophys. Res. Commun.,* 141, 956–962 (1986); Ueda et al., *J. Biol. Chem.,* 262, 505–508 (1987); and Ueda et al., *PNAS,* 84, 3004–3008 (1987)). In the presence of added cytotoxic drug (e.g., as used for cancer chemotherapy), this allows a cell containing the vector to survive, whereas a cell that contains wild-type virus, such as HIV, does not. Such cytotoxic drugs include, but are not limited to, actinomycin D, vinblastine sulfate, vincristine sulfate, daunomycin, adriamycin, VP-16, and AMSA.

Alternatively, such a nucleic acid sequence desirably comprises a sequence selected from the group consisting of a sequence of (or a sequence that encodes) a mutated (i.e., mutant) protease, and a sequence of (or a sequence that encodes) a mutated (i.e., mutant) reverse transcriptase. Preferably, a mutated reverse transcriptase is engineered to be resistant to nucleoside and non-nucleoside reverse transcriptase inhibitors, and a mutated protease is engineered to be resistant to commonly employed protease inhibitors.

Administration of these protease or reverse transcriptase inhibitors to a host in conjunction with the vector is employed to select for cells producing the vector as opposed to cells producing the wild-type virus. Similarly, this approach is modified for use with any drug that inhibits viral replication such that the virus can be mutated to escape from inhibition. Accordingly, for treatment of HIV, the selective nucleic acid sequence incorporated into the vector preferably comprises mutated HIV sequences. Optimally, however, these sequences do not prevent superinfection with wild-type HIV.

Preferably, the vector is one of those set forth above, and, in particular, the preferred crHIV vectors depicted in FIGS. 1B–1E, i.e., crHIV-1.1, crHIV-1.11, crHIV-1.12, and crHIV-1.111, respectively (Dropulic' et al., *PNAS,* 93, 11103–11108 (1996)). Also preferred is a vector as described in Example 11, i.e., cr2HIV.

The cr2HIV vector preferably lacks the tat gene and its splice site from the genome of a wild-type human immunodeficiency virus. In place of the tat gene and its splice site, the cr2HIV vector comprises a triple anti-Tat ribozyme cassette, wherein the catalytic domain of each ribozyme of the triple ribozyme cassette cleaves a different site on a wild-type HIV nucleic acid molecule. Preferably, the catalytic domain of each ribozyme of the triple ribozyme cassette cleaves a different site within tat on a wild-type HIV nucleic acid molecule. More preferably, the catalytic domain of each ribozyme cleaves a nucleotide sequence in a region of a nucleic acid molecule of wild-type HIV for which there is no ribozyme-resistant counterpart in the vector, itself.

Optimally, a vector is compatible with the cell into which it is introduced, e.g., is capable of imparting expression on the cell of the vector-encoded nucleic acid sequences. Desirably, the vector comprises an origin of replication functional in the cell. When a nucleic acid sequence is transferred in the form of its DNA coding sequence (e.g., versus in the form of a complete gene comprising its own promoter), optimally the vector also contains a promoter that is capable of driving expression of the coding sequence and that is operably linked to the coding sequence. A coding sequence is "operably linked" to a promoter (e.g., when both the coding sequence and the promoter together constitute a native or recombinant gene) when the promoter is capable of directing transcription of the coding sequence.

In a recombinant vector of the present invention, preferably all the proper transcription (e.g., initiation and termination signals), translation (e.g., ribosome entry or binding site and the like) and processing signals (e.g., splice donor or acceptor sites, if necessary, and polyadenylation signals) are arranged correctly on the vector, such that any gene or coding sequence is appropriately transcribed (and/or translated, if so desired) in the cells into which the vector is introduced. The manipulation of such signals to ensure appropriate expression in host cells is well within the knowledge and expertise of the ordinary skilled artisan.

Preferably, the vector also comprises some means by which the vector or its contained subcloned sequence is identified and selected. Vector identification and/or selection is accomplished using a variety of approaches known to those skilled in the art. For instance, vectors containing particular genes or coding sequences preferably are identified by hybridization, the presence or absence of so-called "marker" gene functions encoded by marker genes present on the vectors, and/or the expression of particular sequences. In the first approach, the presence of a particular sequence in a vector is detected by hybridization (e.g., by DNA—DNA hybridization) using probes comprising sequences that are homologous to the relevant sequence. In the second approach, the recombinant vector/host system is identified and selected based upon the presence or absence of certain marker gene functions such as resistance to antibiotics, thymidine kinase activity, and the like, caused by particular genes encoding these functions present on the vector. In the third approach, vectors are identified by assaying for a particular gene product encoded by the vector. Such assays are based on the physical, immunological, or functional properties of the gene product.

Accordingly, the present invention also provides a vector, which, if DNA, comprises a nucleotide sequence selected from the group consisting of SEQ ID NOS: 2, 4, 5, 6, 7, 15, 16, 17 and 18 and, which, if RNA, comprises a nucleotide sequence encoded by a nucleotide sequence selected from the group consisting of SEQ ID NOS: 2, 4, 5, 6, 7, 15, 16, 17 and 18.

The present invention further provides a method of engendering a vector, which is derived from a wild-type human immunodeficiency virus and which is capable of replicating only in a host cell that is permissive for replication of said vector, with a ribozyme. The ribozyme, which is comprised within or encoded by the vector, cleaves a nucleic acid of a wild-type human immunodeficiency virus but not the vector, itself, and its transcripts, if any. The method comprises obtaining a vector, which is derived from a wild-type human immunodeficiency virus and which is capable of replicating only in a host cell that is permissive for replication of said vector, and incorporating into the vector a nucleic acid sequence, which comprises or encodes a ribozyme, the catalytic domain of which cleaves a nucleic acid of a wild-type human immunodeficiency virus but not the vector, itself, and its transcripts, if any. In such a method, the nucleotide sequence comprising or encoding the U5 sequence of the wild-type human immunodeficiency virus can be deleted from the vector and replaced with a nucleotide sequence selected from the group consisting of SEQ ID NOS: 2, 6, 7, 15, 16, 17 and 18, if the vector is DNA, and a nucleotide sequence encoded by a nucleotide sequence selected from the group consisting of SEQ ID NOS: 2, 6, 7, 15, 16, 17 and 18, if the vector is RNA. Preferably, the vector replicates in a host cell permissive for replication of said vector more than once.

Also provided by the present invention is a method of modifying a vector. The method comprises obtaining a vector and introducing into the vector a nucleotide sequence selected from the group consisting of the DNA sequences of SEQ ID NOS: 2, 4, 5, 6, 7, 15, 16, 17 and 18, if the vector is DNA, and a nucleotide sequence encoded by a nucleotide sequence selected from the group consisting of SEQ ID NOS: 2, 4, 5, 6, 7, 15, 16, 17 and 18, if the vector is RNA.

Further provided by the present invention is a method of propagating and selectively packaging a conditionally replicating vector without using a packaging cell line. The method comprises contacting the conditionally replicating vector with a cell capable of being infected by another vector, which is the same type of vector as the conditionally replicating vector and which differs from the conditionally replicating vector by being wild-type for replication competency; subsequently contacting the cell with the other vector; and then culturing the cell under conditions conducive to the propagation of the conditionally replicating vector.

Also provided is an isolated and purified nucleic acid molecule selected from the group consisting of a DNA molecule comprising a nucleotide sequence selected from the group consisting of SEQ ID NOS: 2, 6, 7, 15, 16, 17 and 18 and a RNA molecule comprising a nucleotide sequence encoded by a nucleotide sequence selected from the group consisting of SEQ ID NOS: 2, 6, 7, 15, 16, 17 and 18.

Method of Use

The above-described vectors preferably are introduced into a host cell for the prophylactic and therapeutic treatment of viral infection, for ease of vector maintenance, as well as for other reasons. Accordingly, the present invention provides a host cell comprising a vector according to the invention. The isolation of host cells, and/or the maintenance of such cells or cell lines derived therefrom in culture, has become a routine matter, and one in which the ordinary skilled artisan is well-versed.

In particular, a vector as described above preferably is employed in the prophylactic and therapeutic treatment of a viral infection, preferably such as where the infection is from a wild-type virus, preferably a wild-type RNA virus, even more preferably, from a wild-type retrovirus, and optimally from a wild-type HIV.

The method comprises contacting a host cell, which is capable of being infected with a wild-type virus, with a conditionally replicating vector, which is capable of being replicated only in a host cell permissive for the replication of the vector, the presence, transcription or translation of which inhibits the replication of the wild-type strain of virus in the host cell. Desirably, the vector replicates more than once and comprises at least one nucleic acid sequence, the possession (i.e., presence, transcription or translation) of which confers a selective advantage in a host cell to the vector over a wild-type strain of virus, which, optimally, is the strain from which the vector was derived.

According to this method, the nucleic acid sequence preferably comprises a nucleotide sequence, which comprises or encodes a genetic antiviral agent, which adversely affects the replication and/or expression of a virus other than said vector. Desirably, the genetic antiviral agent is selected from the group consisting of an antisense molecule, a ribozyme, and an immunogen. Optimally, the genetic antiviral agent is a ribozyme, preferably the catalytic domain of which cleaves at a 3' nucleotide NUH sequence (i.e., especially a GUC sequence; SEQ ID NO:3). Optionally, the ribozyme is encoded, at least in part, by a sequence selected from the group consisting of SEQ ID NO:4 and SEQ ID NO:5. Desirably, the ribozyme cleaves in a region of the wild-type strain of virus or its transcripts, but does not cleave in a region of the vector or its transcripts. Preferably, this is because the wild-type strain of virus comprises a sequence encoded by SEQ ID NO:1, whereas the vector, if DNA, comprises a nucleotide sequence selected from the group consisting of SEQ ID NOS:2, 6, 7, 15, 16, 17, and 18, and, if RNA, comprises a nucleotide sequence encoded by a nucleotide sequence selected from the group consisting of SEQ ID NOS:2 6, 7, 15, 16, 17 and 18.

The method also desirably is carried out wherein the vector comprises at least one nucleic acid sequence, the possession (i.e., presence, transcription or translation) of which confers a selective advantage to a host cell infected with the vector over a cell infected with a wild-type strain of virus, which, optimally, is the strain of virus from which the vector was derived. In this regard, a vector can comprise at least one nucleic acid sequence, which confers a selective advantage to a host cell infected with the virus and at least nucleic acid sequence, which confers a selective advantage to the vector over a wild-type strain of a virus corresponding to the virus from which the vector was derived.

Accordingly, the method preferably is carried out wherein the nucleic acid sequence comprises a nucleotide sequence encoding a multidrug resistance. Alternatively, the method is carried out wherein the nucleic acid sequence comprises a nucleotide sequence encoding a mutated (mutant) protease and a nucleotide sequence encoding a mutated (mutant) reverse transcriptase, such as when the viral infection to be prophylactically or therapeutically treated is a retrovirus.

The method preferably further comprises administering to a host cell an agent selected from the group consisting of a cytotoxic drug, a protease inhibitor, and a reverse transcriptase inhibitor (i.e., in addition to administration of the vector).

Accordingly, a vector can be employed in accordance with the above-described method not onlv to treat therapeutically a viral infection but to protect a potential host cell from viral infection, i.e., a method of prophylactically treating a viral infection or a "vaccination" against a virus of interest, such as a RNA virus, in particular a retrovirus, such as HIV. The method essentially inhibits the replication of a wild-type strain of virus before the host cell comes into contact with the wild-type strain of virus. In this regard, the vector can comprise or encode proteins that block superinfection with a wild-type virus. The method comprises contacting the host cell with a conditionally replicating vector, as described above, and a "helper-expression vector," i.e., a viral genome that promotes the replication of the "vector" in an uninfected host. The conditionally replicating vector comprises a selective advantage for packaging and/or propagation. Furthermore, the vector, for example, can contain a sequence that enhances cell survival, promotes viral production, induces apoptosis, facilitates protein production and/or promotes immune function and/or targeting. The "helper-expression vector" construct is any expression vector that complements for the inability of the "vector" to replicate. Such helper-expression vectors are common and are easily constructed by those of 7 ordinary skill in the art. The helper-expression vector can be either packaged into virions, like the vector, or expressed without a packaging requirement. Since the "vector" has a selective advantage for packaging and/or propagation, this system provides a safe means to achieve high replication of the virus without the possible pathogenic effects that a live attenuated virus could potentially cause. In addition, the vector can be admixed with nonspecific adjuvants to increase immunogenicity. Such adjuvants are known to those skilled in the art, and include, but are not limited to Freund's complete or incomplete adjuvant, emulsions comprised of bacterial and mycobacterial cell wall components, and the like.

When a vector is employed in accordance with the above-described method as a prophylactic treatment of viral infection, the vector can encode an antigen of a protein that is not encoded by a wild-type virus, such as a mutant viral protein or a nonviral protein. Accordingly, the antigen encoded by the vector can be of bacterial origin or cancerous cell origin, for example. Furthermore, the "vector" also can encode a MHC gene for proper presentation of the antigen to the host's immune system. Thus, such vectors can be used to facilitate a persistent immunological response against a diverse array of potential pathogens and/or endogenous proteins (e.g., tumor-specific antigen) that are selectively expressed in abnormal cells.

Furthermore, the "helper-virus" (also referred to herein as "helper") expression vector can be engineered to express only in specific cell types (e.g., stem cells, professional antigen presenting cells, and tumor cells) by the addition or omission of a specific genetic element/factor (either in the vector or helper-virus expression construct), which permits cell-specific vector replication and spread. Thus, the vector still spreads by complementation with the helper-virus construct, but this spread is cell-specific, depending upon whether a certain genetic element/factor is added to or omitted from the vector or helper-virus expression construct. This can be used alone or in combination with other of the above-mentioned strategies.

For example, a conditionally replicating HIV vector can be designed to replicate specifically in macrophages, rather than in T-cells. The vector, which would constitute a Tat-defective HIV (the vector encodes the other HIV proteins but they are not expressed because of the absence of the Tat transcriptional transactivator), can encode a ribozyme that cleaves wild-type HIV but not conditionally replicating HIV RNA. The helper-expression vector for this vector can encode a tat gene expressed off of a macrophage-specific promoter. Thus, the crHIV would conditionally replicate only in macrophage cells, while not being able to replicate in T-cells or other cell types.

Alternatively, the tat gene can be operably linked to a tumor-specific promoter; thus, the crHIV would then replicate only in tumor CD4 cells and not in normal CD4 cells. The genetic element/factor also can be a modification of a promoter sequence of the vector such that it is expressed only in specific cell types and not in other cells types in concert with the "helper-virus" expression construct.

In another embodiment, the helper-expression construct or the vector construct envelope proteins (if such constructs are engineered to contain envelope proteins) can be modified so that the vector-virion will specifically infect certain cell types (e.g., tumor cells), while not being able to infect other cell types (e.g., normal cells). In yet another embodiment, an adenovirus, which is lacking one or several key factors for replication, could be complemented by using a helper construct, which provides such factors linked to a tumor-specific promoter. Thus, the factors that complement replication of the adenovirus would only be expressed in tumor cells, thereby permitting viral replication in tumor cells (with expression of proteins required for cell killing), but not in normal cells.

Thus, the present invention also provides a method of treating cancer, and in particular, treating T-cell leukemia. "Treating cancer" according to the invention comprises administering to a host a further modified vector as set forth herein for the purpose of effecting a therapeutic response. Such a response can be assessed, for example, by monitoring the attenuation of tumor growth and/or tumor regression. "Tumor growth" includes an increase in tumor size and/or the number of tumors. "Tumor regression" includes a reduction in tumor mass.

"Cancer" according to the invention includes cancers that are characterized by abnormal cellular proliferation and the absence of contact inhibition, which can be evidenced by tumor formation. The term encompasses cancer localized in tumors, as well as cancer not localized in tumors, such as, for instance, those cancer cells that expand from a tumor locally by invasion, or systemically by metastasis. Theoretically, any type of cancer can be targeted for treatment according to the invention. Preferably, however, the cancer is of viral origin.

Finally, the above-described vectors can be directly used for in vivo gene therapy. Current strategies for gene therapy suffer because they cannot mediate gene delivery to large percentage of cells; only a certain percentage of the cells are infected. This is especially important in anti-tumor strategies where gene transduction of the entire tumor population is crucial. By adding the "vector" in concert with a "helper," the immediately transduced-cells will produce viral particles that can infect neighboring cells and thus enable high and possible complete transduction efficiency. In one embodiment to this invention, a human retrovirus (which could be HIV or a retrotransposon element) could be delivered into tissue (or cells in vitro) with a "helper" construct. Cells immediately containing the vector and helper will produce virus and will package the vector conditionally into virions. These virions will be able to mediate high efficiency transduction of neighboring cells (since cell-cell contact is the most efficient means to transduce cells). The immediately transduced cells may or may not die, depending whether the vector/helper combination results in a cytolytic infection. In the case of a retrotransposon, the helper may not need to contain structural proteins since normal or tumor cells may contain the protein/factor necessary for encarpsidation into virions. In this case the helper can merely be, but not restricted to, a transactivator protein that activates transcription of the factors required for retrotransposon encapsidation. In the case of HIV, other factors may, but not necessarily, be required for encapsidation of the HIV genome into progeny virions for infection/transduction of cells.

The above-described vectors also can be used in counter-biological and counter-chemical warfare strategies. For example, a conditionally replicating vector can be delivered into an individual recently infected with a highly pathogenic virus or bacterium or a chemical agent (e.g., toxin). The vector would interfere with the replication of the pathogenic virus as described previously. However, the conditionally replicating vector also can be used for antibacterial or anti-chemical strategies in concert with a helper-expression vector ("helper").

For example, a conditionally replicating vector can secrete anti-bacterial or anti-toxin antibodies after a "helper" permits its expression and propagation. The "helper" can be, but not necessarily, driven off an inducible promoter that permits its expression upon activation by a bacterium, a cytokine (in response to bacterial infection), an antibiotic (as with the tetracycline inducible promoter systems (Paulus et al., *J. Virol.*, 70, 62–67 (1996)) or a chemical (e.g., the toxin, itself). Thus, the conditionally replicating vector would not only selectively propagate with the aid of the "helper" in response to the incurring pathogen or toxin (as a result of activation of the helper) but also secrete anti-pathogen or anti-toxin antibodies to inhibit the pathological effects of the tumor antigen, pathogen or chemical (e.g., toxin). Thus, any protein, factor, or genetic element that can be transcribed into either mRNA and/or protein can be inserted into a conditionally replicating vector to inhibit a pathogenic response—in c-oncer.t wich a "helper," whi.ch promotes its selective propagation and expression (selective because the products of the helper are expressed conditionally (for example, but not restricted to, (a) an inducible promoter system—a factor in a tumor cell activates the production of a helper factor, a toxin responsive sequence that expresses a helper factor, or a cytokine responsive promoter induces production of a helper factor, (b) a helper RNA/protein/factor is selectively stabilized in certain cells and not in others), and (c) indirect induction of a third party gene that affects helper viral protein production, chaperoning, targeting, structure or another biofunction). Such strategies can be used in transgenic plants and animals to protect them from pathogens. Similarly, such strategies can be used in transgenic systems to produce heterologous proteins/factors of value.

In another embodiment of a method in accordance with the present invention, a cell line can be developed for screening a drug/factor to determine, for example, which part of the protein/factor is important for a particular function. A vector can be created to express a mutagenized protein of interest within a given cell line. The RNA encoding the mutagenized protein, however, is made resistant to the ribozyme by insertion of silent point mutations, for example. Wild-type protein expression, however, is inhibited within the cell line. Vectors that express a ribozyme to the protein of interest also can be constructed to express mutant test protein. When the vector is transduced into the cells, most of the native RNA encoding the normal protein is cleaved, whereas the mutant test protein is expressed. This method can be used with recently developed delivery and selection techniques as a quick and powerful technique to determine how a given protein functions and how a given factor/drug interacts with the protein.

There also are numerous uses of the method and the vectors of the present invention in vitro. For instance, the vectors can be employed to ascertain certain nuances of viral replication and ribozyme function. Similarly, the ribozyme-containing vectors can be used as diagnostic tools, e.g., to assess mutations present in diseased cells, or to examine genetic drift. This aforementioned discussion is by no means comprehensive regarding the use of the present invention.

Benefits of the Invention

The advantages of using a crHIV strategy for genetic therapeutic treatment of AIDS and other viruses are considerable. For instance, the problem of targeting the vector to cells infected by HIV becomes resolved. After in vivo transfection of crHIVs into infected CD4+ cells, the crHIVs become packaged into progeny virions using the endogenous infectious HIV envelope proteins. Thus, the crHIV RNA tags along inside progeny virions and infects cell types that are normally infectable by that particular strain of HIV, producing nonpathogenic virions. This includes difficult to target cells, such as the microglia of the brain, which are a major reservoir for HIV infection of the central nervous system. There is likely to be little toxicity associated with crHIV vectors that infect uninfected CD4+ cells, since no viral proteins are coded by crHIV vectors. Moreover, the result of crHIV vector competition with wild-type HIV results in the production of nonpathogenic particles, which results in decreased viral loads. Decreasing pathogenic HIV-1 loads can not only increase the survival time of infected individuals, but also can decrease the rate of transmission to uninfected individuals, since the crHIV particles also can spread systemically (i.e., as does infectious HIV). Decreased pathogenic HIV-1 loads in the blood can be particularly important in pregnant HIV-infected individuals, since the production of crHIVs can also decrease transmission of HIV-1 from infected mothers to their fetuses in utero The plasrrid DNA/lipid mixture that can be employed for introducing the crHIV vector into host cells should be stable and cheap to produce, bypassing expensive ex vivo strategies. Of course, the method of the invention is inherently flexible inasmuch as it could also be employed for ex vivo gene delivery, should this be desired. Regardless, the availability of the liposome-mediated approach opens the possibility for treatment of the general population—something that is not feasible with current gene therapeutic strategies. The crHIV vectors also can be engineered to contain several ribozymes, which can be made to different targets on the HIV genome. This reduces the possibility that infectious HIV can mutate and escape the effect of the anti-HIV ribozymes. Furthermore, the conditionally replication competent virus strategy can be applied to treat other viral infections, especially those where viral turnover is high.

A particularly useful feature of crHIV vectors is that they can be employed to express genetic antiviral agents, for instance, a ribozyme, post-transcriptionally. Thus, infection of uninfected cells with crHIV vectors results in low toxicity because little expression occurs from the HIV long-terminal repeat (LTR) promoter in the absence of the Tat protein. High levels of crHIV expression, and its consequent antiviral activity, occurs only when the Tat protein is provided by complementation with wild-type HIV. Thus, crHIV vectors are not designed to protect cells from HIV infection, but to lower the overall wild-type HIV viral burden through selective accumulation of nonpathogenic crHIV particles.

While not seeking to be bound by any particular theory regarding the operation or functioning of the invention, it is believed that ribozymes can be employed as confirmed in the following Examples to provide crHIV genomes with a selective advantage because of two useful properties: (1) they have a high degree of specificity, and (2) they have a relative efficiency, depending upon their ability to co-localize with target RNAs (Cech, *Science*, 236, 1532–1539 (1987)). The specificity of ribozymes is conferred by their specific hybridization to complementary target sequences containing a XUY site. Ribozymes are relatively efficient because they cleave target RNAs with high efficacy only when they efficiently co-localize with target RNAs. In a mixed HIV/crHIV infection, co-localization of ribozyme-containing crHIV RNAs with wild-type HIV RNAs must occur, since HIV RNA genomes dimerize prior to packaging into progeny virions. Cleavage of non-genomic species of wild-type HIV RNAs, required for the production of viral proteins, is likely to be less efficient than that of genomic wild-type HIV RNAs inasmuch as non-genomic HIV RNAs no not dimerize. It was discovered in the experiments described herein that the selective advantage conferred to crHIV RNAs was due to the selective packaging of crHIVs into viral particles. These results suggest that most efficient cleavage occurs intracellularly during dimerization, resulting in the selective destruction of wild-type HIV RNAs by host nucleases. This allows for the preferential packaging of crHIV RNAs into viral particles.

The application of crHIV vectors for HIV therapy can involve not only genomic selection of crHIVs, but also cellular selection of cells producing crHIV particles. Otherwise, the cells producing wild-type HIVs will produce wild-type HIV particles at a selective advantage over the cells producing crHIV particles, and will rapidly predominate. A selective advantage can be conferred to crHIV expressing cells by inserting a gene into crHIV genomes (e.g., the multidrug resistance gene) that confer crHIV expressing cells (in the presence of drug) with a survival advantage over cells expressing wild-type HIV. Under these conditions, wild-type HIV-expressing cells progressively die, but still produce some wild-type HIV, while crHIV-expressing cells that selectively produce crHIV survive. Infection of crHIV- containing cells with remaining wild-type HIV will result in the further production of crHIV containing viral particles. Thus, a viral genomic shift can result with the cumulative infection of CD4+ cells with crHIV genomes, thereby altering the viral balance in the host from pathogenic wild-type HIV to nonpathogenic crHIV genomes. Such a strategy can result in clearance of wild-type HIV, once the balance of HIV genomes selectively shifts from wild-type HIV to crHIV. Viral replication eventually ceases, since crHIVs can only replicate in the presence of wild-type HIV helper genomes. Therefore, under such mutually restrictive conditions, it can be possible to engineer crHIV vectors that not only decrease wild-type HIV viral loads, but also clear the virus from the HIV-infected host.

Means of Administration

According to the invention, a vector is introduced into a host cell in need of gene therapy for viral infection as previously described. The means of introduction comprises contacting a host capable of being infected with a virus with a vector according to the invention. Preferably, such contacting comprises any means by which the vector is introduced into a host cell; the method is not dependent on any particular means of introduction and is not to be so construed. Means of introduction are well-known to those skilled in the art, and also are exemplified herein.

Accordingly, introduction can be effected, for instance, either in vitro (e.g., in an ex vivo type method of gene therapy) or in vivo, which includes the use of electroporation, transformation, transduction, conjugation or triparental mating, transfection, infection, membrane fusion with cationic lipids, high-velocity bombardment with DNA-coated microprojectiles, incubation with calcium phosphate-DNA precipitate, direct microinjection into single cells, and the like. Other methods also are available and are known to those skilled in the art.

Preferably, however, the vectors or ribozymes are introduced by means of cationic lipids, e.g., liposomes. Such liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (e.g., as reviewed in PCT patent application no. WO 95/21259) can be employed in the present invention. For liposome administration, the recommendations identified in the PCT patent application no. WO 93/23569 can be followed. Generally, with such administration the formulation is taken up by the majority of lymphocytes within 8 hr at 37° C., within more than 50% of the injected dose being detected in the spleen an hour after intravenous administration. Similarly, other delivery vehicles include hydrogels and controlled-release polymers.

The form of the vector introduced into a host cell can vary, depending in part on whether the vector is being introduced in vitro or in vivo. For instance, the nucleic acid can be closed circular, nicked, or linearized, depending on whether the vector is to be maintained extragenomically (i.e., as an autonomously replicating vector), integrated as a provirus or prophage, transiently transfected, transiently infected as with use of a replication-deficient or conditionally replicating virus, or stably introduced into the host genome through-double or single crossover recombination events.

Prior to introduction into a host, a vector of the present invention can be formulated into various compositions for use in therapeutic and prophylactic treatment methods. In particular, the vector can on made into) a pharmaceutical composition by combination with appropriate pharmaceutically acceptable carriers or diluents, and can be formulated to be appropriate for either human or veterinary applications.

Thus, a composition for use in the method of the present invention can comprise one or more of the aforementioned vectors, preferably in combination with a pharmaceutically acceptable carrier. Pharmaceutically acceptable carriers are well-known to those skilled in the art, as are suitable methods of administration. The choice of carrier will be determined, in part, by the particular vector, as well as by the particular method used to administer the composition. One skilled in the art will also appreciate that various routes of administering a composition are available, and, although more than one route can be used for administration, a particular route can provide a more immediate and more effective reaction than another route. Accordingly, there are a wide variety of suitable formulations of the composition of the present invention.

A composition comprised of a vector of the present invention, alone or in combination with other antiviral compounds, can be made into a formulation suitable for parenteral administration, preferably intraperitoneal administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit dose or multidose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

A formulation suitable for oral administration can consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

An aerosol formulation suitable for administration via inhalation also can be made. The aerosol formulation can be placed into a pressurized acceptable propellant, such as dichlorodifluoromethane, propane, nitrogen, and the like.

Similarly, a formulation suitable for oral administration can include lozenge forms, that can comprise the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

A formulation suitable for topical application can be in the form of creams, ointments, or lotions.

A formulation for rectal administration can be presented as a suppository with a-suitable base comprising, for example, cocoa butter or a salicylate. A formulation suitable for vaginal administration can be presented as a pessary, tampon, cream, gel, paste, foam, or spray formula containing, in addition to the active ingredient, such carriers as are known in the art to be appropriate. Similarly, the active ingredient can be combined with a lubricant as a coating on a condom.

The dose administered to an animal, particularly a human, in the context of the present invention should be sufficient to effect a therapeutic response in the infected individual over a reasonable time frame. The dose will be determined by the potency of the particular vector employed for treatment, the severity of the disease state, as well as the body weight and age of the infected individual. The size of the dose also will be determined by the existence of any adverse side effects that can accompany the use of the particular vector employed. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a vector, alone or in combination with other antiviral agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "antiviral effective amount" or an amount necessary to achieve an "effective level" in the individual patient.

Since the "effective level" is used as the preferred endpoint for dosing, the actual dose and schedule can vary, depending on interindividual differences in pharmacokinetics, drug distribution, and metabolism. The "effective level" can be defined, for example, as the blood or tissue level desired in the patient that corresponds to a concentration of one or more vector(s) according to the invention, which inhibits a virus, such as HIV, in an assay predictive for clinical antiviral activity of chemical compounds. The "effective level" for compounds of the present invention also can vary when the compositions of the present invention are used in combination with zidovudine or other known antiviral compounds or combinations thereof.

One skilled in the art can easily determine the appropriate dose, schedule, and method of administration for the exact formulation of the composition being used, in order to achieve the desired "effective level" in the individual patient. One skilled in the art also can readily determine and use an appropriate indicator of the "effective level" of the compounds of the present invention by a direct (e.g., analytical chemical analysis) or indirect (e.g., with surrogate indicators of viral infection, such as p24 or reverse transcriptase for treatment of AIDS or AIDS-like disease) analysis of appropriate patient samples (e.g., blood and/or tissues).

Further, with respect to determining the effective level in a patient for treatment of AIDS or AIDS-like disease, in particular, suitable animal models are available and have been widely implemented for evaluating the in vivo efficacy against HIV of various gene therapy protocols (Sarver et al. (1993b), supra). These models include mice, monkeys and cats. Even though these animals are not naturally susceptible to HIV disease, chimeric mice models (e.g., SCID, bg/nu/xid, bone marrow-ablated BALB/c) reconstituted with human peripheral blood mononuclear cells (PBMCs), lymph nodes, or fetal liver/thymus tissues can be infected with HIV, arid employed as models for HIV pathogenesis and gene therapy. Similarly, the simian immune deficiency virus (SIV)/monkey model can be employed, as can the feline immune deficiency virus (FIV)/cat model.

Generally, an amount of vector sufficient to achieve a tissue concentration of the administered ribozyme (or vector) of from about 50 to about 300 mg/kg of body weight per day is preferred, especially of from about 100 to about 200 mg/kg of body weight per day. In certain applications, e.g., topical, ocular or vaginal applications, multiple daily doses are preferred. Moreover, the number of doses will vary depending on the means of delivery and the particular vector administered.

In the treatment of some virally infected individuals, it can be desirable to utilize a "mega-dosing" regimen, wherein a large dose of a vector is administered, time is allowed for the compound to act, and then a suitable reagent is administered to the individual to inactivate the active compound(s). In the method of the present invention, the treatment (i.e., the replication of the vector in competition with the virus being treated) is necessarily limited. In other words, as the level, for instance, of HIV decreases, the level of vector dependent on HIV for production of virions will also decrease.

The pharmaceutical composition can contain other pharmaceuticals, in conjunction with a vector according to the invention, when used to therapeutically treat AIDS. These other pharmaceuticals can be used in their traditional fashion (i.e., as agents to treat HIV infection), as well as more particularly, in the method of selecting for crHIV viruses in vivo. Such selection as described herein will promote conditionally replicating HIV spread, and allow conditionally replicating HIV to more effectively compete with wild-type HIV, which will necessarily limit wild-type HIV pathogenicity. In particular, it is contemplated that an antiretroviral agent be employed, such as, preferably, zidovudine. Further representative examples of these additional pharmaceuticals that can be used in addition to those previously described, include antiviral compounds, immunomodulators, immunostimulants, antibiotics, and other agents and treatment regimes (including those recognized as alternative medicine) that can be employed to treat AIDS. Antiviral compounds include, but are not limited to, ddI, ddC, gancylclovir, fluorinated dideoxynucleotides, non-nucleoside analog compounds such as nevirapine (Shih et al., *PNAS,* 88, 9878–9882 (1991)), TIBO derivatives such as R82913 (White et al., *Antiviral Research,* 16, 257–266 (1991)), and BI-RJ-70 (Shih et al., *Am. J. Med.,* 90 (Suppl. 4A), 8S–17S (1991)). Immunomodulators and immunostimulants include, but are not limited to, various interleukins, CD4, cytokines, antibody preparations, blood transfusions, and cell transfusions. Antibiotics include, but are not limited to, antifungal agents, antibacterial agents, and anti-*Pneumocystis carinii* agents.

Administration of the virus-inhibiting compound with other anti-retroviral agents and particularly with known RT inhibitors, such as ddC, zidovudine, ddI, ddA, or other inhibitors that act against other HIV proteins, such as anti-TAT agents, will generally inhibit most or all replicative stages of the viral life cycle. The dosages of ddC and zidovudine used in AIDS or ARC patients have been published. A virustatic range of ddC is generally between 0.05 $\mu$M to 1.0 $\mu$M. A range of about 0.005–0.25 mg/kg body weight is virustatic in most patients. The dose ranges for oral administration are somewhat broader, for example 0.001 to 0.25 mg/kg given in one or more doses at intervals of 2, 4, 6, 8, and 12; etc., hr. Preferably, 0.01 mg/kg body weight ddC is given every 8 hr. When given in combined therapy, the other antiviral compound, for example, can be givers at the same time as a vector according to the invention, or the dosing can be staggered as desired. The vector also can be combined in a composition. Doses of each can be less, when used in combination, than when either is used alone.

EXAMPLES

The present inventive compounds and methods are further described in the context of the following examples. These examples serve to illustrate further the present invention and are not intended to limit the scope of the invention.

Example 1

This example describes the construction of conditionally replication competent vectors according to the invention. In particular, this example describes the construction of conditionally replicating vectors based on HIV, i.e., crHIV vectors.

One of the most prominent aspects of HIV-1 pathogenesis is the production of genetic variants of the virus. The rapid production of HIV variants in vivo indicates that the virus can be considered within the framework of Darwinian genetic modeling (see, e.g., Coffin, *Curr. Top. Microbiol. Immunol.,* 176, 143–164 (1992); and Coffin, *Science,* 267, 483–489 (1995)). The variants are a result of the infidelity of the HIV-1 reverse transcriptase molecule, which creates mutations in newly transcribed proviruses from viral genomic RNA. Therefore, under in vivo conditions of no significant bottlenecks and many replicative cycles, a substantial degree of genetic variation occurs with the production of many viral variants. Yet, wild-type HIV still predominates, since, under such unrestricted conditions, it has the highest selective advantage. However, in the presence of an inhibitor, for instance zidovudine, a viral variant will be selected that is conferred with a higher selective advantage than the wind-type strain, and consequently will predominate (Coffin (1992) and (1995), supra). Based on this, the present invention provides a conditionally replicating viral vector strategy that affords nonpathogenic HIV-1 genomes with a selective advantage over pathogenic wild-type HIV-1.

These nonpathogenic, conditionally replicating HIV (crHIV) vectors are defective HIVs that undergo replication and packaging only in cells that are infected with wild-type HIV. crHIV genomes compete with and decrease pathogenic wild-type HIV viral loads. The effect of decreasing wild-type HIV viral loads in an infected host should lead to an increased life expectancy. It should also decrease the ability of infected hosts to transmit wild-type HIV to uninfected individuals. For successful competition of crHIVs with wild-type HIV-1, two factors appear important: (1) a selective advantage of crHIV genomes over wild-type HIV genomes, and (2) a selective advantage of crHIV-expressing cells over cells expressing wild-type HIV (i.e., a selective advantage for the production of crHIV virions from crHIV-expressing cells over cells expressing wild-type HIV).

The crHIV vectors conditionally replicate due to the fact that they contain the sequences required for RNA expression, dimerization and packaging, but do not express functional (i.e., wild-type) HIV-1 proteins. A selective advantage was imparted to the crHIV vectors by inserting a ribozyme cassette that cleaves in the U5 region of the wild-type HIV genome, but not the crHIV U5 RNA.

The ribozymes present in the vectors do not cleave the crHIV RNA because the U5 region of the crHIV RNA has been modified by conserved base substitution (base substitutions present in other HIV strains) to prevent the ribozymes from efficiently binding and cleaving these sites. Moreover, the crHIVs are nonpathogenic because they do not code for proteins believed to be responsible for CD4+ cell death. When the HIV-infected cells (that have been transfected with the crHIV vector) become activated, the cells become capable of complementing the crHIV genomic deficits, resulting in the production of crHIV progeny virions.

In general, crHIV genomes were constructed from the full-length, infectious HIV clone, pNL4-3 (Adachi et al., *J. Virol.,* 59, 284–291 (1986)). All cloning reactions and DNA, RNA, and protein manipulations were carried out using methods well known to the ordinary skilled artisan, and which have been described in the art, e.g., Maniatis et al., *Molecular Cloning: A Laboratory Manual,* 2nd ed. (Cold Spring Harbor Laboratory, NY (1982)). Enzymes and reagents employed in these reactions were obtained from commercial suppliers (e.g., New England Biolabs, Inc., Beverly, Mass.; Clontech, Palo Alto, Calif.; and Boehringer Mannheim, Inc., Indianapolis, Ind.) and were used according to the manufacturers' recommendations. Moreover, vector maintenance and propagation was done using techniques that are commonly known, and that have been described previously (e.g., Dropulic' et al. (1992), supra; and Dropulic' et al. (1993), supra).

pNL4-3 was cleaved with the enzymes Pst I (which cleaves in gag, at about position +1000 from the start of transcription) and Xho I (which cleaves in nef, at about position +8400 from the start of transcription), and a polylinker containing convenient restriction sites was inserted. A 0.86 kb Bgl II to Bam HI fragment containing the rev responsive element (RRE) was cloned into a Bam HI site present in the polylinker. These manipulations resulted in deletion of the HIV wild-type genome from within the gag coding region to within the U3 coding region (i.e., thus also deleting the nef gene). While the vector is able to produce a truncated gag transcript, a full-length functional Gag protein is not produced by the vector. However, inasmuch as wild-type Gag functions are unnecessary according to the invention, the gag sequences can be mutated to prevent Gag protein from being translated.

A ribozyme cassette containing either single or multiple ribozymes as described herein was inserted into a Sal I site downstream from the Bam HI site. To accomplish this, complementary deoxyoligonucleotides encoding ribozyme sequences were synthesized, annealed and then cloned into the Sal I site. The ribozymes employed for construction of the crHIV vectors were hammerhead ribozymes. These ribozymes contained a catalytic domain comprised of 22 base pairs, and two hybridization domains comprised of 9 base pairs each. The ribozymes were targeted either to the +115 or +133 site (i.e., corresponding to the number of base pairs downstream from the start of transcription) of the U5 RNA sequence. The hybridization domains and catalytic domain (underlined) of the ribozymes targeted to the +115 site and the +133 site are as follows:

CACACAACACTGATGAGGCCGAAAGGC-CGAAACGGGCACA ("the +115 ribozyme")[SEQ ID NO:4]

ATCTCTAGTCTGATGAGGCCGAAAGGC-CGAAACCAGAGTC ("the +133 ribozyme")[SEQ ID NO:5]

Figure 1B:
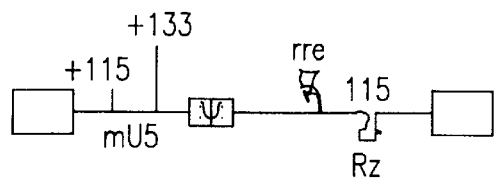
Figure 1C:
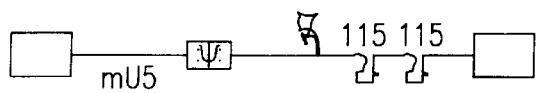
Figure 1E:
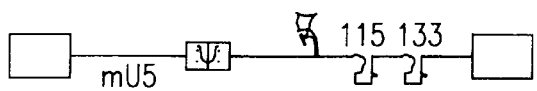
Figure 1E:
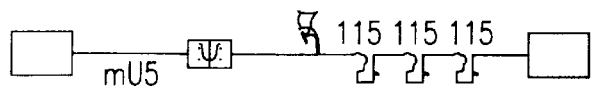

The ribozyme cassette was comprised of either a single, double or triple ribozyme(s) placed in tandem. Vectors containing either single (i.e., "crHIV-1.1" vector, FIG. 1B) or triple (i.e. "crHIV-1.1" vector, FIG. 1E) ribozymes were targeted to the same site of the U5 HIV RNA, at position +115. Vectors containing double ribozymes were targeted either to the same site at position +115 (i.e., "crHIV-1.11" vector, FIG. 1C), or to different sites at positions +115 and +133 of the U5 HIV RNA; crHIV-1.12 (i.e., "crHIV-1.12" vector, FIG. 1D). These vectors are referred to herein generically as "crHIV" vectors.

To complete the construction of the vectors, the crHIV vectors were rendered resistant to ribozyme cleavage (i.e., in their manifestation as RNA) by mutating a site recognized by the hammerhead ribozymes occurring within the U5 region of the crHIV genome. To accomplish this, a double-stranded oligonucleotide (i.e., AAGCTTGCCTTGAGT-GCTCAAAGTAGTGTGTGCCCACCTGT-TGTGTGACTCTGGCAG
CTAGAGATCCCACAGACCCTTTTAGT-CAGTGTGGAAAATCTCTAGCAGTGGCGCC [SEQ ID NO:14]) containing the base substitutions depicted in FIG. 2 [SEQ ID NO:2] was used to introduce modified sites into the vector. Specifically, base substitutions were engineered into the ribozyme hybridization and cleavage sites at base pairs 115 and 133. In particular, as illustrated in FIG. 2; mutations were introduced at base pairs 113, 114, 132, 134 and 142. These sites can be modified to comprise any mutation (i.e., GTGTGCCCNNCTGTTGTGTGACT CTGGNANCTAGAGANC, wherein N can be any nucleotide [SEQ ID NO:15]). Preferably, however, the sequences are mutated such that there is, for instance, a G to A substitution at site +113 (i.e., such that the sequence comprises GTGTGCCCATCTGTTGTGTGACTCTGG-TAACTAGAGATC [SEQ ID NO:16]), a U (i.e., T, in terms of the DNA sequence) to C substitution at site +114 [SEQ ID NO:6], a U (i.e., T, in terms of the DNA sequence) to C substitution at site +132 [SEQ ID NO:7], an A to G substitution at site +134 (i.e., such that the sequence comprises GTGTGCCCGTCTGTTGT-GTGACTCTGGTAGCTAGAGATC [SEQ ID NO:17]) and a U (i.e., T, in terms of the DNA sequence) to A substitution at site +142 (i.e., such that the sequence comprises GTGT-GCCCGTCTGTTGTGTGACTCTGGTAACTAGAGAAC [SEQ ID NO:18]), which mutations can be made either alone, or in combination. In particular, in the absence of other U5 mutations, the U (i.e. T, in terms of the DNA sequence) to C substitution at site +114 [SEQ ID NO:6] and/or site +132 [SEQ ID NO:7] in the crHIV U5 RNA prevents its scission by ribozymes (Uhlenbeck (1987), supra). The inserted base-substitutions are present in various other strains of HIV (Myers et al., HIV Sequence Database, Los Alamos Nat. Lab. (1994)), which indicates that these substitutions do not decrease the replicative capacity of the HIV genome.

The method as set forth herein can be employed to construct other conditionally replicating vectors, for instance, comprised of differing viral genomes (e.g., different RNA viruses), or comprised of different genetic antiviral agents. Furthermore,. a conditionally replicating vector can be further modified to impart to a host cell, into which the vector is introduced, a selective advantage over a host cell containing the wild-type virus. For instance, such a vector can be modified to further encode multidrug resistance, or a mutated protease or reverse transcriptase.

Example 2

This example describes the resistance to ribozyme cleavage of conditionally replicating vectors, and, in particular, of the crHIV vectors.

To confirm the resistance to ribozyme cleavage of the crHIV vectors, in vitro transcription was performed. To accomplish this, the ribozyme sequences were cloned into the Xho I site of pBluescript KSII (Stratagene, La Jolla, Calif.). A 0.21 kilobase pair (kb) Bgl II fragment containing the mutated crHIV U5 region similarly was excised from the crHIV vector and inserted into the Bam HI site of pBluescript KSII. The resultant modified pBluescript KSII vectors were linearized with Bss HII prior to in vitro transcription. A similar plasmid expressing wild-type HIV U5 RNA (described in Myers et al. (1994), supra) was employed as a control. It was linearized with Eco RI prior to in vitro transcription.

Radiolabeled U5 HIV RNA and ribozyme RNA were produced by in vitro transcription of the vectors, as previously described (Dropulic' et al. (1992), supra). The radio-labeled transcripts were incubated together (at a target to ribozyme molar ratio of 1:2) in 1X transcription buffer containing 40 mM Tris-HCl, pH 7.5, 6 MM $MgCl_2$, 2 mM Spermidine, and 10 mM NaCl. The samples were heated to 65° C., and then cooled to 37° C. for 5 min prior to the addition of stop buffer solution containing 95% formamide, 20 mM EDTA, 0.05% Bromophenol Blue, and 0.05% Xylene Cyanol FF. The products were then resolved by denaturing polyacrylamide gel electrophoresis (PAGE), and detected by autoradiography.

Figure 3:
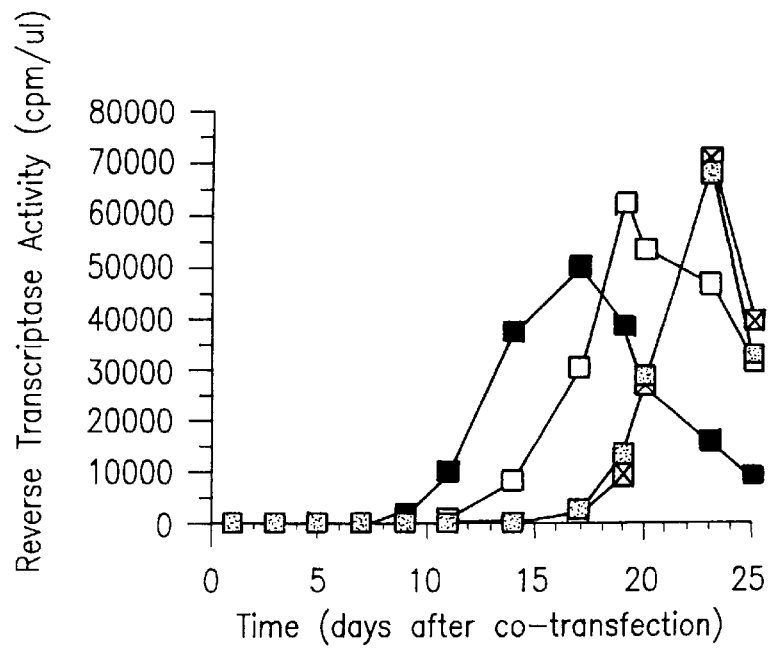
FIG. 3 is an autoradiograph depicting the susceptibility to in vitro ribozyme cleavage of wild-type U5 RNA (lanes 1–7) as compared with no cleavage of crHIV U5 RNA (lanes 8–14): wild-type HIV U5 RNA transcript (lane 1); ribozyme RNA containing a single ribozyme targeted to the +115 site (i.e., corresponding to the number of base pairs downstream from the start of transcription) (lanes 2 & 9); wild-type HIV U5 RNA incubated with a single ribozyme targeted to site +115 resulting in cleavage products P1 and P2 (lane 3); ribozyme RNA containing a double ribozyme targeted to the +115 site (lanes 4 & 11); wild-type HIV RNA incubated with a double ribozyme targeted to the +115 site (lane 5); ribozyme RNA containing a double ribozyme targeted to sites +115 and +133 (lanes 6 & 13); wild-type HIV RNA incubated with a double ribozyme targeted to sites +115 and +133 (lane 7); crHIV U5 RNA transcript (lane 8); and crHIV U5 RNA incubated with either a single or a double ribozyme targeted to site +115 (lanes 10, 12 & 14), which showed no cleavage. The asterisks indicate where the ribozyme cleavage products would resolve, if present.

As can be seen in FIG. 3, when wild-type U5-HIV RNA (FIG. 3, lane 1) was incubated with a transcript containing a single ribozyme to site +115 (FIG. 3, lane 2), cleavage was readily observed (FIG. 3, lane 3). Such cleavage results in products PI and P2. Cleavage also can be seen when wild-type HIV RNA was incubated with RNAs containing double ribozymes to either the same site (FIG. 3, lanes 4 &

5), or to different sites (FIG. 3, lanes 6 & 7). When a ribozyme-containing transcript directed to two different sites was incubated with wild-type HIV RNA, products P1, P2 and 23 were produced. P3 results from cleavage at the +133 site.

In comparison, when the modified U5-containing crHIV RNA (FIG. 3, lane 1) was incubated with either a single ribozyme directed to the +115 site, or double ribozyme directed to either the +115 site or the +133 site, cleavage products were not detected (FIG. 3, lanes 10, 12, and 14). Thus, these results confirm that crHIV U5 RNAs are resistant to ribozyme cleavage, while wild-type HIV-U5 RNAs are cleaved by anti-U5 ribozymes. Moreover, the results validate that the approach of the present invention can be employed to impart conditionally replicating vectors (including vectors other than crHIV vectors) with a selective advantage for replication when introduced into a host cell as compared with a wild-type strain of virus.

Example 3

This example describes the ability of ribozyme-containing conditionally replicating vectors to cleave wild-type viral RNA intracellularly. In particular, this example describes the ability of crHIV vectors to cleave wild-type HIV RNA intracellularly.

The effectiveness of crHIV vector-mediated inhibition of wild-type HIV was tested by co-transfecting the genomes into Jurkat cells. Transfection was carried out by washing about 10⁶ Jurkat cells in Opti-MEM medium (Life Technologies, Gibco BRL, Gaithersburg, Md.) and then co-transfecting the cells with about 0.6 μg of wild-type HIV DNA (i.e., pNL4-3) and about 1.8 μg of crHIV DNA. A molar ratio of wild-type HIV to crHIV provirus of about 1:3 was used to ensure that all cells transfected with wild-type HIV also contained crHIV proviruses. DNA was mixed in lipofectin solution (Life Technologies) for 30 min, and then was incubated with Jurkat cells for about 3 to about 6 hr, after which complete RPMI 1640 medium containing 10% fetal bovine serum (FBS) was added. Virus-containing supernatants were harvested every 2 to 4 days, and virus levels were assayed by reverse transcriptase activity in cell supernatants, as previously described (Dropulic' et al. (1992), supra)

Figure 4:
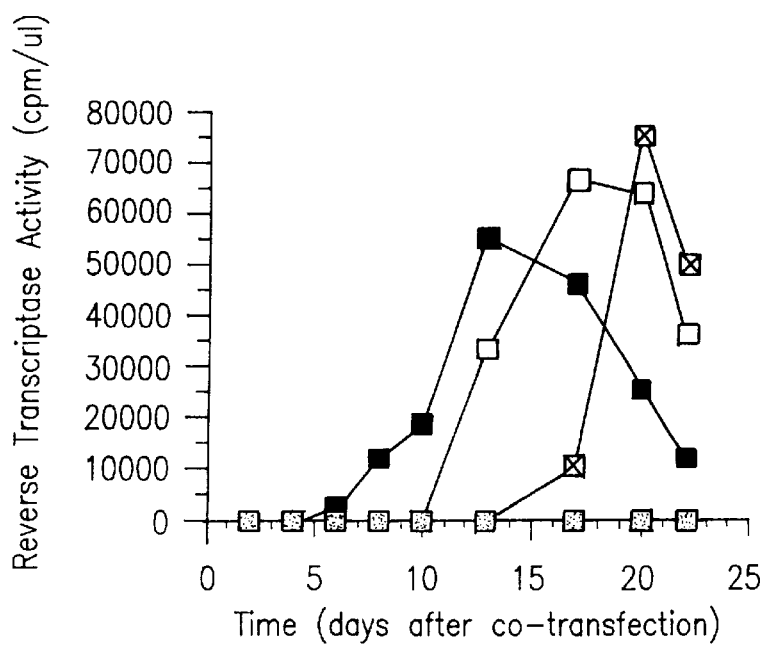
FIG. 4 is a graph depicting reverse transcriptase activity (cpm/µl) versus time (days after co-transfection) for crHIV mediated inhibition of wild-type HIV replication in Jurkat cells co-transfected with wild-type HIV and crHIV-1.1 (open boxes), with wild-type HIV and crHIV-1.11 (open crossed boxes), with wild-type HIV and crHIV-1.12 (stippled boxes), and with wild-type HIV and control plasmid pGEM-3Z (solid boxes).

The effect of crHIV genomes on wild-type HIV replication is shown in FIG. 4. When wild-type HIV was co-transfected with crHIV-1.1, viral growth was delayed (FIG. 4, open boxes) relative to cells co-transfected with wild-type HIV and a control virus (FIG. 4, closed boxes), but was not inhibited. Since anti-U5 ribozymes can inhibit HIV replication in vivo under co-localized conditions (e.g., Dropulic' et al. (1992), supra), the viral growth seen could be the result of either: (a) preferential packaging for wild-type HIV RNAs into progeny virions, (b) the production of wild-type HIV RNAs that are resistant to ribozyme cleavage, or (c) an accumulation of nonfunctional ribozymes in crHIV RNAs.

The nature of "escape" viral growth was tested by co-transfecting wild-type HIV with crHIV vectors that contain double ribozymes. If preferential packaging of wild-type HIV is responsible for viral growth, then cultures containing double ribozyme crHIVs should have similar growth kinetics as cultures containing single ribozyme crHIVs. If, however, viral growth results from wild-type HIV RNAs that have become resistant to ribozyme action (i.e., as a result of viral reverse transcriptase infidelity), then the kinetics of viral growth should show a greater delay for cultures containing crHIV-1.12 (i.e., directed against two viral sites) as compared with cultures containing crHIV-1.11 (i.e., directed against a single viral site). Alternatively, if a delay in viral growth was seen that was comparable in cultures containing the different double ribozyme-containing crHIVs, this would suggest that a proportion of the singly expressed ribozymes are nonfunctional in vivo.

As can be seen in FIG. 4, cultures containing crHIV-1.11 (FIG. 4, open crossed boxes) or crHIV-1.12 (FIG. 4, stippled boxes) showed a greater delay in the onset of viral growth than crHIV-1.1, which contained a singly transcribed ribozyme (FIG. 4, open boxes). However, the delay in the onset of viral growth between crHIV-1.11 and crHIV-1.12 was similar, indicating the correctness of the third possibility, i.e., that singly transcribed ribozymes are kinetically less efficient in cleaving target RNAs than are double ribozymes. This suggests that a certain proportion of intracellularly transcribed ribozymes can form in a nonfunctional, possibly misfolded, conformation, since the co-transfection experiments were performed in a molar excess of ribozyme-containing crHIV genomes.

Figure 5A:
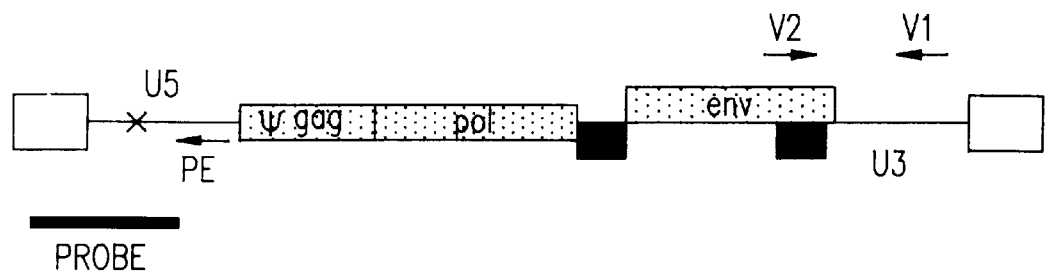
FIG. 5 is a graph depicting reverse transcriptase activity (cpm/µl) versus time (days after co-transfection) for crHIV-mediated inhibition of wild-type HIV replication in Jurkat cells co-transfected with wild-type HIV and crHIV-1.1 (open boxes), wild-type HIV and crHIV-1.11 (open crossed boxes), wild-type HIV and crHIV-1.111 (stippled boxes), and wild-type HIV and plasmid pGEM-3Z (solid boxes).
Figure 5B:
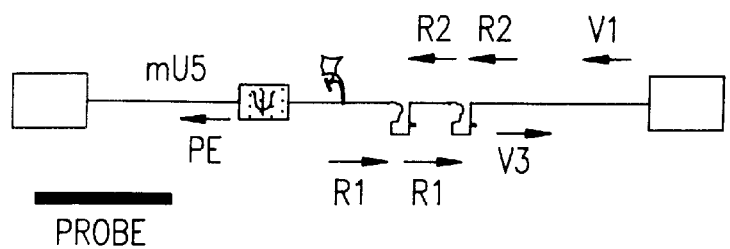
Figure 5C:
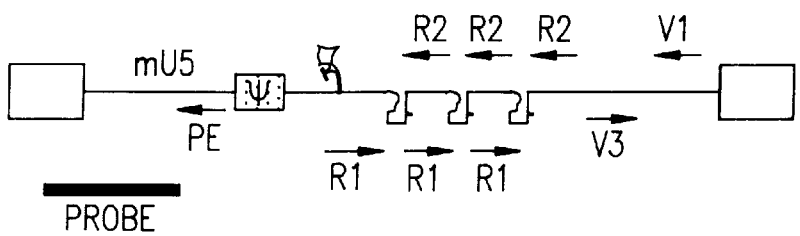

The ability of multiple ribozymes to relieve this kinetic limitation by providing a greater probability for functional ribozymes to associate with wild-type HIV RNAs was explored. For these experiments, Jurkat cells were co-transfected with wild-type HIV and crHIV-1.111, which contains a triple ribozyme to site +115. As can be seen in FIG. 5 (stippled boxes), there is no evidence of viral growth with use of a triple ribozyme, even after 22 days in culture. These results are particularly significant in view of the fact that normal primary T cells often die shortly (e.g., about a week) after infection with HIV.

Moreover, these results confirm that ribozyme-containing conditionally replicating vectors, such as the crHIV vectors, and particularly those that contain multiple ribozymes, can be employed to compete intracellularly with a wild-type viral genome, such as HIV.

Example 4

This example describes an investigation of the mechanism underlying the ability of ribozyme-containing conditionally replicating vectors, particularly crHIV vectors, to cleave wild-type viral RNA intracellularly.

Figure 6A:
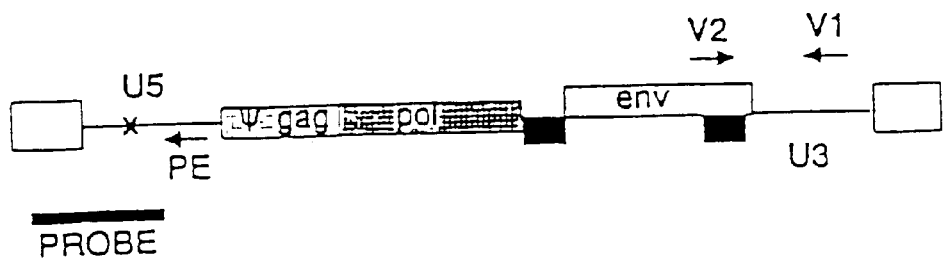
FIGS. 6A–6C are schematic depictions of the primers and probes employed to detect U5 RNA transcripts from wild-type HIV (FIG. 6A), crHIV-1.1 (FIG. 6B), and crHIV-1.111 (FIG. 6C). Designations: U5, U5 coding sequence; Ψ, packaging signal; gag, pol and env, the coding sequences for proteins that form the viral core, reverse transcriptase, and envelope, respectively; open boxes, viral long terminal repeats; solid boxes, tat and rev coding sequences; and PE, V1, V2, V3, R1 and R2, primers employed for wild-type and/or conditionally replicating viruses. The cross in the wild-type U5 coding region indicates the approximate region in which ribozymes according to the invention cleave in the wild-type U5 RNA, but not modified crHIV U5 RNA (i.e., "mU5").
Figure 6B:
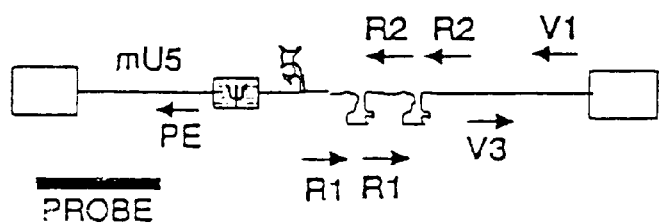
Figure 6C:
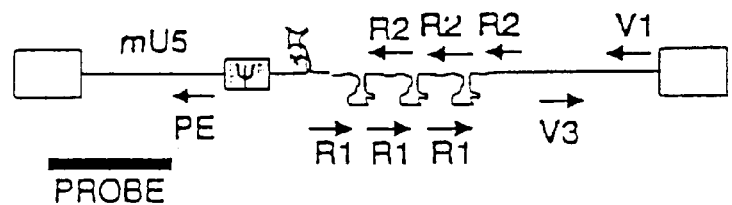

For these experiments, cell supernatant RNA from wild-type HIV and crHIV-1.111 co-transfected cultures was examined with use of the reverse transcription polymerase chain reaction (RT-PCR), as described herein. RT-PCR was done using the primers depicted in FIGS. 6A–C. Namely, ribozyme RNA was detected using primers R1 and R2, wild-type HIV RNA was detected using primers V1 and V3, and crHIV RNA was detected using primers V2 and V3. Primers R1 (TGTGACGTCGACCACACAACACTGATG [SEQ ID NO:8]) and R2 (TGTGACGTCGACTCTAGATGTGCCCGTTTCGGC [SEQ ID NO:9] each comprise a Sal I restriction site, and amplify the anti-U5 ribozyme RNA by binding to the ribozyme hybridization sequences. In crHIV-1.111 expressing cells, single, double and triple ribozyme amplification products are seen. Primers VI (GGTTAAGCTTGAATTAGCCCCTTCCAGTCCCC [SEQ ID NO:10]) and V2 (GGTTGGATCCGGGTGGCAAGTGGTCAAAAAG [SEQ ID NO:11]) each comprise Bam HI or Hin dIII restriction sites, and amplify wild-type HIV RNAs. Along with the aforementioned V1 primer, the V3 (CGGATCCACGCGTGTCGACGAGCTCCCATGGTGA TCAG [SEQ ID NO:12]) primer comprises Bam HI and other restriction sites. This primer set amplifies crHIV-RNAs from a crHIV-specific polylinker sequence.

To perform RT-PCR, virion and intracellular RNAs were isolated using Trizol™ (Life Technologies) Intracellular viral RNAs were isolated directly from microcentifuged cell pellets. Virion RNAs were isolated from culture supernatants that were first cleared of cells and debris by microcentrifugation at 12,000×g for 5 min. Trizol™ was added to the cell-free supernatants, and the mixtures were incubated for 5 min prior to the addition of chloroform for phase separation. The aqueous phase was transferred to a fresh tube, and the RNA was precipitated with isopropanol using glycogen. After reconstitution of the RNA pellet, the viral RNAs were reverse-transcribed and then amplified by PCR using radiolabeled primers.

Reverse transcription was performed for 1 hr at 42° C. in first-strand buffer containing 50 mM Tris-HCl, pH 8.3, 75 mM KCl, 3 MM $MgCl_2$, 5 mM DTT, 1 mM dNTPs, and 20 units (U) of RNase inhibitor, to which 25 U of MuLV Reverse Transcriptase was added. After reverse transcription was completed, the reverse transcriptase was heat-inactivated at 65° C. for 10 min. The entire mixture was then added directly to PCR buffer to comprise a mixture containing a final concentration of 10 mM Tris-HCl, pH 8.3, 50 mM KCl, and 1.5 MM $MgCl_2$. The mixture was amplified for 30 cycles using 2.5 U of Taq enzyme. The radiolabeled PCR products were then resolved by denaturing PAGE, and detected by autoradiography.

Figure 7:
FIG. 7 is an autoradiograph depicting RT-PCR amplification using R1 and R2 primers of ribozyme RNAs from virions produced from day +20 cultures of Jurkat cells co-transfected with wild-type HIV and crHIV-1.111 (lane 4), or transfected with only wild-type HIV (lane 2). Lanes 1 and 3 comprise RT-PCR negative controls, wherein RNA was mock reverse-transcribed in the absence of reverse transcriptase.
Figure 7:
Figure 7:
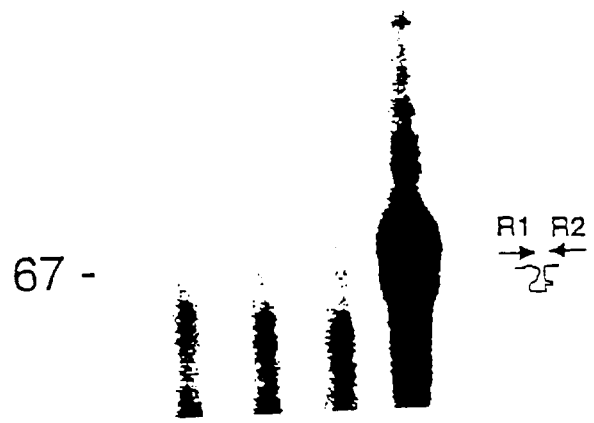

As can be seen in FIG. 7 (lane 4), crHIV-1.111 ribozyme RNAs exist in the supernatants of cells more than twenty days after co-transfection with wild-type HIV-1 and crHIV-1.111 proviral genomes. This is evidenced by the existence of single, double and triple ribozyme RNA PCR products. In comparison, no such products are seen in virions produced by control wild-type, HIV-transfected cultures (lane 2). During this period, the cells appeared normal, with no apparent signs of crHIV-induced cytotoxicity. This confirms that crHIVs are packaged into viral particles even though no reverse transcriptase activity was observed. Moreover, this indicates that crHIVs can be complemented intracellularly by HIV gene functions.

Thus, these results indicate that crHIVs inhibit wild-type HIV replication by inhibiting wild-type HIV spread. The results further indicate that other conditionally replicating vectors, for instance, other viral vectors, and/or vectors containing other genetic antivirals can similarly be employed to inhibit wild-type viral replication and spread.

Example 5

This example describes a further exploration of the mechanism underlying the ability of ribozyme-containing, conditionally replicating vectors, particularly crHIV vectors, to cleave wild-type, viral RNA intracellularly.

One possible mechanism is that both wild-type HIV and crHIV RNAs are packaged into progeny virions, and efficient cleavage occurs in this small viral volume due to co-localization of ribozyme and target RNAs. Alternatively, selective packaging of crHIV RNAs into progeny virions can occur because cleavage of wild-type HIV RNAs predominantly occurs intracellularly, and not in the HIV virion. These mechanisms were explored herein.

Figure 8:
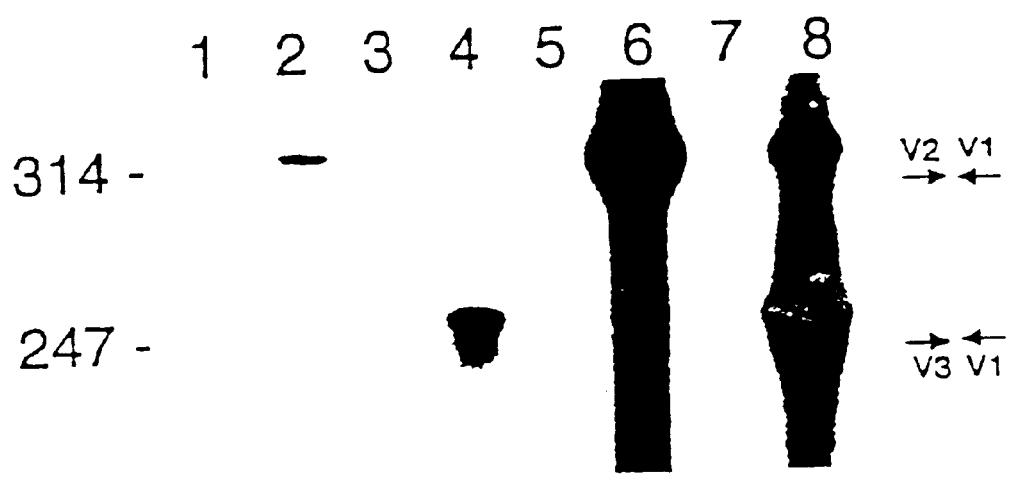
FIG. 8 is an autoradiograph depicting virion (lanes 1–4) and intracellular (lanes 5–8) RT-PCR amplification using V1, V2 and V3 primers of viral RNAs from day +20 cultures of Jurkat cells co-transfected with wild-type HIV and crHIV-1.111 (lanes 4 and 8), or transfected with wild-type HIV (lanes 2 and 6) alone. Lanes 1, 3, 5 and 7 comprise RT-PCR negative controls.

The means by which crHIV-1.111 inhibited wild-type HIV spread was examined by RT-PCR of virion- and cell-associated viral RNAs, in cell cultures transfected with wild-type HIV alone (FIG. 8, lanes 2 and 6), or co-transfected with wild-type HIV and crHIV-1.111 (FIG. 8, lanes 4. and 8). crHIV-1.111 RNAs were exclusively present in progeny virions produced following co-transfection (FIG. 8, lane 4). In comparison, control, wild-type, HIV-transfected cultures produced virions that contained only wild-type HIV RNAs (FIG. 8, lane 2). Intracellularly, both wild-type HIV and crHIV-1.111 RNAs were evident in co-transfected cultures (FIG. 8, lane 8). Therefore, although both wild-type HIV and crHIV RNAs are synthesized intracellularly, crHIV RNAs are selectively packaged into progeny virions. This suggests that crHIV-1.111 inhibited wild-type HIV spread by selectively cleaving genomic wild-type HIV RNAs prior to encapsidation, while allowing some sub-genomic wild-type RNAs to be translated into proteins for virion production.

To test whether genomic wild-type RNAs are selectively cleaved by crHIV RNAs, the types of intracellular RNAs present in Jurkat cell cultures obtained about 20 days following co-transfection was examined by Northern hybridization. The probe employed for the Northern blot analysis, as indicated in FIG. 6, was isolated from a 0.21 kb Bgl II fragment from the U5 region of pNL4-3.

Figure 9:
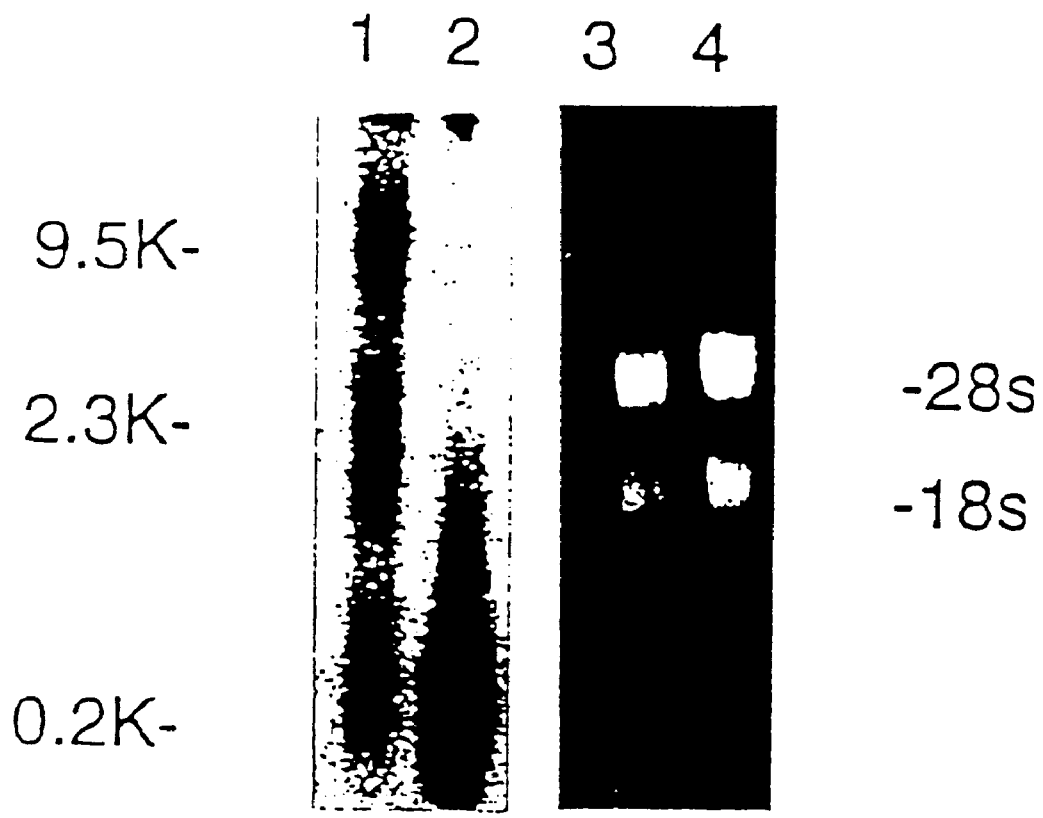
FIG. 9 is an autoradiograph depicting a Northern blot analysis of intracellular HIV RNAs from day +20 cultures of Jurkat cells co-transfected with wild-type HIV and crHIV-1.111 (lane 4), or transfected with wild-type HIV (lane 3) alone. The quality of the RNA preparation and the amount loaded is shown for wild-type HIV RNA (lane 3) and crHIV-1.111 RNA (lane 4).

Results of these experiments are indicated in FIG. 9. Cultures transfected with wild-type HIV express all wild-type HIV RNA species, i.e., genomic and subgenomic RNA species (FIG. 9, lane 1). In comparison, crHIV-1.111 co-transfected cultures do not express significant amounts of genomic (9.7 kb), wild-type HIV RNA (FIG. 9, lane 2). RNAs of low molecular weight (reflecting the presence of subgenomic wild-type HIV RNAs) were observed in co-transfected cultures (FIG. 9, lane 2). The HIV-RNA smearing in these samples suggests that some degraded genomic HIV RNAs may be present within these low molecular-weight RNAs. In comparison, the smearing of wild-type HIV RNA from control, wild-type HIV cells (FIG. 9, lane 1) is due to RNA degradation that occurs from the significant CPE observed at the late stage of HIV infection.

Accordingly, these results confirm that genomic, wild-type HIV RNAs are selectively cleaved and degraded in cells containing wild-type HIV and crHIV-1.111 genomes, allowing selective crHIV RNA packaging into virions. Furthermore, these results indicate that the method may similarly be employed with other viruses, particularly with other RNA viruses.

Example 6

This example describes an investigation of the ability of ribozyme-containing, conditionally replicating vectors, particularly crHIV vectors, to undergo the complete viral replicative cycle in the presence of wild-type helper virus.

To confirm that crHIV genomes undergo the complete viral replicative cycle in the presence of a helper wild-type HIV genome, the production of virus particles containing crHIV genomes was examined under several conditions. Specifically, first the production of viral particles containing crHIV genomes was examined in activated ACH2 cells (AIDS Reagent Reference Program, Rockville, Md.). These cells comprise a latently HIV-1 infected cell line. Next, the ability of any crHIV particles derived from these cultures to infect uninfected Jurkat cells and produce crHIV DNA was examined.

Figures 10A, 10B, 10C:
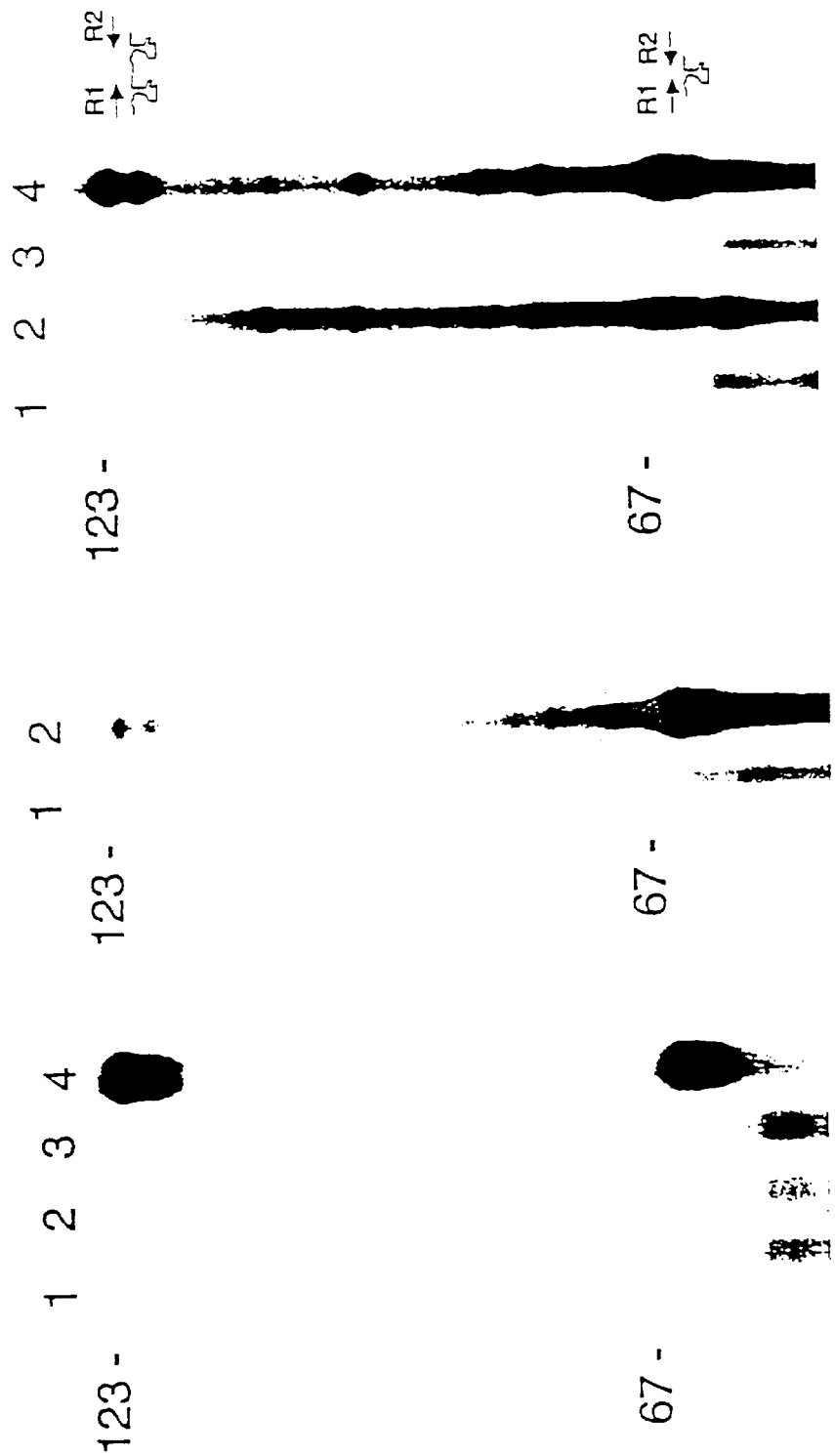
FIGS. 10A–10C are autoradiographs depicting the replication of crHIVs in the presence of wild-type HIV helper.

For these experiments, about $10^6$ ACH2 cells were transfected with about 2.5 µg of vector DNA. The cells were stimulated with 50 nM 12-O-tetradecanoylphorbol 13-acetate (TPA) about 24 hr after transfection. RNA was isolated from the cell supernatants about 72 hr after transfection. RT-2CR was performed using the R1 and R2 primers as described in Example 4. As can be seen in FIG. 10A, crHIV ribozyme RNAs ware detected in virions produced by activated ACH2 cells after transfection with crHIV-1.11 (lane 4), but not after transfection with pGEM 3Z control plasmid (Promega, Madison, Wis.) (lane 2). Therefore, transfection of crHIV vectors into infected CD4+ cells results in the production of viral particles that contain crHIV RNAs.

The ability of crHIV virions derived from these cultures to infect uninfected Jurkat cells and produce crHIV proviruses was examined next. Such proviruses were detected by isolating cellular DNA using Trizol™, cleaving the DNA with Eco RI, and then amplifying ribozymal DNA by PCR, using the R1 & R2 primers as described in Example 4. FIG. 10B illustrates the production of crHIV DNA in Jurkat cells after infection of cell supernatants derived from crHIV-transfected ACH2 cells. Namely, in this case, specific amplification of crHIV-1.11 ribozymal DNA was seen (FIG. 10B, lane 2). In comparison, cells infected with stimulated ACH2 cell supernatants alone (i.e., in the absence of any infection of ACH2 cells with crHIV-1.111) showed no ribozymal DNA products (FIG. 10C, lane 1).

Since crHIV vectors spread only in the presence of wild-type helper HIV genomes, the ability of uninfected cells containing crHIV genomes to be rescued after infection with wild-type HIV was examined. These experiments were carried out by first transfecting cells with crHIV-1.11 (i.e., as representative of the crHIV vectors), and then superinfecting with wild-type HIV (i.e., pNL4-3). Accordingly, about 106 Jurkat cells were transfected with about 2.5 $\mu$g of crHIV DNA. The cells were allowed to grow for about 72 hr prior to infection with wild-type HIV stock virus. crHIV-1.11 transfected Jurkat cells were incubated with stock pNL4-3 (2×105 TCID50 units per 106 cells) for about 2 hr at 37° C., washed three times in Opti-MEM® I Reduced Serum Medium, and then resuspended in complete medium (RPMI 1640 with 10% FBS). RNA was isolated from cell supernatants as described in Example 4 about 5 days after infection.

For the $TCID_{50}$ assay, supernatants containing HIV were plated out on 96-well plates by 5-fold limiting dilution. About $10^4$ MT4 cells (AIDS Reagent Reference Program, Rockville, Md.; and Harada et al., *Science*, 229, 563–566 (1985)) were then added to the diluted viral suspensions and the resultant suspensions were incubated for 7 days until complete viral growth had occurred. MT4 cells are modified T-cells that contain the Tax gene from HTLV-1, which is a transactivator gene that is analogous to Tat in HIV-1. Supernatants were then assayed for reverse transcriptase activity and scored as previously described (Dropulic' et al. (1992), supra). The tissue culture infectious dose ($TCID_{50}$) was determined by the method of Reed and Muench (*In: Tech. in HIV Res.*, Johnson et al., eds., Stockton Press, 71–76 (1990)).

Superinfection of crHIV-transfected Jurkat cells with wild-type HIV resulted in crHIV genomes being rescued into viral particles (FIG. 10C, lane 4). The crHIV genomes are packaged into viral particles after superinfection with wild-type HIV. During this period, the cells appeared normal, with no significant signs of cytotoxicity.

These results confirm that crHIV genomes are able to undergo the full replicative cycle after complementation with wild-type HIV helper virus. These results also confirm that other viral genomes are likely able to undergo the full replicative cycle after complementation with the corresponding wild-type virus.

Example 7

This example describes the nature of escape viral growth reported in the prior examples.

Figure 11:
FIG. 11 is an autoradiograph depicting RT-PCR using the viral-specific primers (V1, V2 & V3) of virion-associated RNAs during the early (lanes 1–4) and late (lanes 5–8) stages of viral growth, of virions from cultures co-transfected with wild-type HIV RNA and crHIV-1.11 (lanes 4 and 8, respectively), or transfected with wild-type HIV alone (lanes 2 and 6, respectively). Lanes 1, 3, 5 and 7 comprise RT-PCR negative controls.

The nature of escape viral growth from cultures transfected with wild-type HIV, or co-transfected with wild-type HIV and crHIV-1.11, was examined by analyzing. virion RNAs using RT-PCR as previously described. Viruses produced by cultures at the early stages of viral growth (i.e., wild-type HIV transfected culture at day +11, crHIV-1.11 co-transfected culture at day +19) contained predominantly crHIV RNAs (FIG. 11; wild-type HIV. transfected culture, lane 2, crHIV-1.11 co-transfected culture, lane 4). In comparison, cultures from the late stages of various growth (i.e., wild-type HIV transfected culture at day +17, crHIV-1.11 co-transfected culture at day +23) contained predominately wild-type HIV RNAs (FIG. 11; wild-type HIV transfected culture, lane 6, crHIV-1.11 co-transfected culture, lane 8). Therefore, viral growth from cells co-transfected with wild-type HIV and crHIV-1.11 proviruses (FIG. 11, lanes 4 and 8) appeared to result from the growth of wild-type HIV that escaped from intracellular ribozyme restriction. Significantly, crHIV genomes still comprised a substantial proportion of the total HIV genomes even in cultures at the late stages of viral growth (FIG. 11, lanes 4 and 8). This suggests that, although wild-type HIV genomes predominated, crHIV genomes were, nevertheless, spreading through the culture, albeit at lower efficiencies than wild-type HIV genomes.

This confirms that the crHIV vectors, as well as further conditionally replicating vectors, can effectively compete with wild-type viral genomes for viral replication.

Example 8

This example further describes the nature of escape viral growth reported in the prior examples.

The effect of crHIV RNA packaging into virions during escape viral growth was studied by measuring infectious wild-type HIV titers. Limiting dilution $TCID_{50}$ assays (as described in Example 6) were performed on viral supernatants from cultures at the exponential stage of viral growth (i.e., wild-type HIV cultures at day +14, crHIV-1.1 cultures at day +16, crHIV-1.11 or crHIV-1.12 cultures at day +20). The samples were normalized prior to assay using reverse transcriptase activity. Supernatants from wild-type HIV, crHIV-1.1, crHIV-1.11 and crHIV-1.12 cultures had an infectious dose of 1.3×104 $TCID_{50}$/ml, 5.4×103 $TCID_{50}$/ml, 3.8×103 $TCID_{50}$/ml, and 3.8×103 $TCID_{50}$/ml, respectively. Thus, the packaging of crHIV RNAs into virions during escape viral growth results in a decrease in the number of infectious wild-type HIV particles that are produced.

Next examined was whether the decrease in infectious wild-type HIV titer was the result of cleavage of wild-type HIV RNAs within escaped virions. RNA cleavage products from virions present in the supernatants of co-transfected cells were assessed by primer extension. The PE primer (GGTTAAGCTTGTCGCCGCCCCTCGCCTCTTG [SEQ ID NC:13]) identified in FIG. 6, and which comprises a Hin dIII restriction site, was employed. Primer extension across the cleavage site was performed for 2 hr at 42° C. in first-strand buffer comprising 50 mM Tris-HCl, pH 8.3, 75 nM KCl, 3 mM $MgCl_2$, 5 mM DTT, 1 mM dNTPs, and 20 U of RNase inhibitor, to which 25 U of MuLV reverse transcriptase was added. Viral RNAs were isolated from concentrated virion preparations derived from crHIV co-transfected cultures. Cells and debris were removed by centrifugation at 2,000×g for 15 min at 4° C. Virus was then concentrated by ultracentrifugation at 30,000×g for 4 hr at 4° C. Viral RNAs were then isolated from the viral pellets using Trizoll as previously described.

Viral RNAs were isolated from wild-type, HIV-transfected and crHIV-1.11 co-transfected culture supernatants during the late stages of viral growth (i.e., wild-type HIV transfected cultures at day +17, crHIV-1.11 co-transfected cultures at day +23). As indicated in FIG. 12: the virions in these cultures contained both wild-type HIV and crHIV genomic RNAs. Full-length, primer-extended cDNA was observed in both wild-type HIV transfected (FIG. 12, lane 1) and crHIV-1.11 co-transfected (FIG. 12, lane 2) cultures. No smaller cDNAs, which would have resulted from U5SRNA cleavage, were detected, despite extensive primer-extension analysis. Thus, the decrease in infectious wild-type HIV titers is not due to intraviral cleavage of wild-type HIV RNAs, but to their numerical displacement by crHIV RNAs within progeny virions.

These results, thus, indicate that the method described herein can be employed to displace wild-type genomes, such as HIV genomes and other genomes, from progeny virions, using the conditionally replicating vectors according to the invention.

Example 9

This example demonstrates that crHIV vectors can inhibit wild-type HIV replication after challenge with plasmid or recombinant crHIV-1.111 virus.

Jurkat cells were infected with stock HIV (clone pNL4-3) and were then challenged with either (1) plasmid DNA containing the crHIV-1.111 construct or (2) recombinant crHIV-1.111 virus packaged in 293 cells, i.e., mutant crHIV-1.M (Nadlini et al., *Science*, 272, 263–267 (1996)). The cells were subjected to DLS lipid-mediated transfection (Thierry et al., *PNAS*, 92, 9742–9746 (1995)) or crHIV-mediated delivery. Viral replication was measured by using the reverse transcriptase assay 12 days after original infection with HIV. Wild-type positive control cultures showed normal levels of wild-type HIV growth. When cells infected with wild-type HIV were challenged with mutant crHIV-1.M via DLS-mediated transfection, wild-type HIV v. 4al growth was unaffected. In contrast, when cells infected with wild-type HIV were challenged with crHIV-1.111, which encodes an anti-HIV ribozyme, via DLS-mediated transfection, wild-type HIV viral growth (i.e., replication) was significantly inhibited. Furthermore, when mutant crHIV-1.M was challenged with wild-type HIV, wild-type HIV replication was unaffected. In contrast, when wild-type HIV was challenged with crHIV-1.111, wild-type HIV replication was significantly inhibited. The data show that crHIV vectors can be used to inhibit significantly wild-type HIV replication intracellularly.

Example 10

This example describes the use of conditionally replicating vectors in the therapeutic treatment of cancer.

The conditionally replicating, cancer-treating, viral vector can be constructed to be defective in its ability to replicate in normal cells because it lacks a viral protein requisite for its replication. However, when this vector infects a cancerous cell, the unique properties of the cancerous cell provide a factor (e.g., preferably the same mutated cellular protein that promotes the aberrant growth of cancerous cells) that facilitates the replication of the defective cancer-treatment vector. Accordingly, this method differs from the method employed for treatment of viral infection inasmuch as selective packaging of the viral vector does not occur, and instead, there is preferential lysis of cancerous cells due to the packaging of progeny vector-derived virions in the cell. However, the method is similar to the method employed for the viral infections in that it can use a helper-virus expression vector to selectively propagate the conditionally replicating vector in cancerous cells. The vector and/or helper-virus expression vector can be made to be responsive to tumor-specific factors, thereby facilitating vector spread selectively in tumor cells.

Tumor-specific factors, which can be exploited in this method of treatment, include, but are not limited to, those that act at the level: (1) of viral entry into cells (e.g., the presence of a tumor-specific receptor that will allow a viral vector to selectively enter a cancerous cell, but not a normal cell); (2) of viral transcription (e.g., a mutant cancerous cell protein will allow a cancer-treatment vector to transcribe selectively its RNA in cancer cells, as opposed to normal cells; and (3) of viral maturation and release (e.g., mutant cancerous cellular proteins can allow the conditionally replicating cancer-treatment vector to selectively mature, for instance, by association of the mutant cellular proteins with the viral proteins or genome, and the resultant promotion of viral maturation and release). Accordingly, mutant proteins that exist in cancerous cells can interact with viral proteins (or the genomic RNA or DNA) at many stages of the viral replication cycle. These interactions can be manipulated to create conditionally replicating cancer-treatment vectors, which are defective in normal cells and can replicate in cancerous cells.

In particular, this method can be employed for the treatment of T-cell leukemia. T-cell leukemias are a severe form of cancer with a poor prognosis. Many of the leukemic T-cells are $CD4^+$. Thus, an anti-T-cell leukemia-treating, conditionally replicating vector can be constructed using wild-type HIV as the vector backbone. Inasmuch as HIV ostensibly enters cells via the CD4 glycoprotein, this vector would act at the level of viral entry into cells.

The vector can be made into a cancer-treatment vector by introducing deletion(s) into wild-type HIV, for example. The HIV genome can be mutated by producing it in its DNA form and conducting site-specific mutagenesis, as previously described. The method similarly can be employed by complementing viral deficits with other tumor suppressor mutations, or negative oncogenes, or by exploiting other tumor-specific factors that interact with viral proteins. For example, the tat gene, which encodes a protein important for HIV replication, can be deleted. In the absence of Tat, HIV can no longer upregulate its expression, which is absolutely essential for HIV propagation. The Tat protein functions by binding to the TAR RNA stem-loop structure, which is associated with the HIV promoter, and is capable of upregulating HIV expression by more than 100-fold. Thus, without Tat, the HIV-based vector will not express HIV proteins, and will not propagate and kill normal (i.e., noncancerous) T-cells.

However, leukemic T-cells typically comprise a functionally altered molecule that is either mutated, overexpressed or silenced. This altered state of molecular function is not associated with normal cells. In its non-mutated state (but not its mutated state), this molecule functions in the regulation of cell proliferation and/or apoptosis (programmed cell death). The changes associated with the mutated state can be used to promote specifically the propagation of a conditionally replicating viral vector. This could be done in the presence or absence of a helper-virus expression vector. For example, the defect in Tat can be complemented by a helper-expression vector that is driven of a tumor-specific promoter, where the promoter is from a gene in leukemic cells that is overexpressed. Such a vector only can replicate in leukemic T-cells and not in normal cells. Viral expression and propagation in leukemic T-cells would result in the lysis and death of the cells with nascent viral production. The vector could also carry additional elements to promote cell killing (e.g., a sequence encoding a toxin, a cytokine or an antigen to promote immune targeting).

Other methods and strategies can similarly be employed in the construction of further conditionally replicating cancer-treatment vectors.

Example 11

This example describes the development of second generation crHIV constructs (cr2HIV), which have better propagation properties than crHIV-1.111 vectors.

The second generation vectors enable increased production of crHIV particles from crHIV-producing cells. The production of more crHIV particles facilitates their spread and prevents wild-type HIV outgrowth in cultures. Lacking sequences encoding proteins that block superinfection with wild-type HIV, the vectors contain all sequences of the native, wild-type HIV but do not encode the Tat gene. In place of the Tat gene is a triple anti-Tat ribozyme cassette ([SEQ ID NO: 19]) made to the three different sites on the Tat gene. Also, the Tat splice site was deleted so that the Tat ribozymes will selectively cleave genomic wild-type HIV RNAs and not spliced wild-type HIV RNAs, which complement for the defect in Tat and facilitate crHIV replication. In contrast to the previous vectors, which do not encode proteins, other than, perhaps; a proteinaceous genetic antiviral agent, such as an immunogen, the second generation vectors encode, but only express, these proteins in the presence of Tat. In a cell that contains both wild-type HIV and crHIV genomes, crHIVs genomes will not only be selectively packaged, but many more virions will be produced than from crHIV-1.111 cells, since the structural proteins are produced not only from wild-type HIV, but from crHIV genomes as well. Accordingly, the vector is conferred with a selective advantage for propagation, since it not only is producing virions from wild-type HIV templates but also from crHIV templates.

The second generation vectors are also characterized by comprising or encoding ribozymes, the catalytic domains of which target regions other than those in the vector, itself. In contrast to crHIV-1.111, which comprises or encodes ribozymes targeted to the $U_5$ region of the HIV leader sequence, which necessitated the incorporation of modified U5 sequences into the leader of the crHIV vector, the ribozymes of the second generation vectors target regions that are not in the vector, itself, thereby eliminating the need to modify the sequence of the vector. This reduces the possibility that resistant HIVs could form by recombination of wild-type HIV with modified crHIV U5 sequences. Thus, recombination of wild-type HIV with crHIV sequences would provide no benefit to the wild-type HIV; incorporation of ribozyme sequences into wild-type HIV would only be detrimental to wild-type HIV.

The second generation vectors are further characterized by the incorporation of a number of different ribozymes, each of which is targeted to a different site, to reduce the possibility of wild-type HIV from forming ribozyme-resistant mutants.

In a further improvement of the vector system for the purposes of a safe, conditionally replicating vaccine, the "helper-vector" construct can be further improved by adding genetic elements/factors that specifically facilitate crHIV replication and spread in a safe manner. One embodiment is the introduction of ribozymes into the helper-vector to prevent its genetic recombination with the vector to produce wild-type virus. Thus, the above cr2HIV vector can be complemented with a Tat helper-expression vector to facilitate its spread. By inserting anti-HIV ribozymes into the helper-expression vector, the chance for recombination is minimized because an encounter of the vector with helper-vector RNA would result in their mutual scission and destruction. Therefore, the helper-expression vector can be modified in a number of ways to aid a particular prophylactic or therapeutic strategy. Accordingly, cr2HIV vectors have utility as vaccines against HIV since they (1) replicate and, thus, persistently stimulate the host's immune response and 12) allow the host to recognize diverse epitopes, since they are derived from HIV and change antigenically.

All of the references cited herein, including patents, patent applications, and publications, are hereby incorporated in their entireties by reference.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following-claims.

What is claimed is:

1. A method of expressing a gene in a host cell, which method comprises:

a) contacting the host cell with:
      (i) a conditionally replicating virus vector which comprises at least one gene to be expressed and further comprises at least a first nucleotide sequence wherein:
         (a) the conditionally replicating vector replicates in said host cell only upon complementation with a wild-type virus, a helper virus, or a helper vector; and
         (b) the conditionally replicating vector is selectively replicated over said wild-type virus, helper virus, or helper vector; and
      (ii) a wild-type virus, a helper virus, or a helper vector, wherein said wild-type virus, helper virus or helper vector is adversely affected by the presence of said first nucleotide sequence;
   or with:
      (i) a helper virus or a helper vector, which comprises at least a first nucleotide sequence, wherein said helper virus or helper vector is not adversely affected by the presence of said first nucleotide sequence; and
      (ii) a conditionally replicating virus vector which comprises at least one gene to be expressed wherein:
         (a) the conditionally replicating vector replicates in a host cell only upon complementation with a wild-type virus, a helper virus, or a helper vector;
         (b) genetic recombination between the conditionally replicating vector and the helper virus or helper vector is reduced by the presence of said first nucleotide sequence; and
         (c) the conditionally replicated vector is selectively replicated over said helper virus or helper vector; and b) expressing said gene in the host cell or in a cell infected with a vector replicated from said conditionally replicating vector in said host cell.

2. The method of claim 1 wherein expressing said gene in said host cell inhibits replication of a wild-type strain of said virus in said cell.

3. The method of claim 1, wherein said first nucleotide sequence comprises or encodes, in which case it also expresses, a genetic antiviral agent.

4. The method of claim 3, wherein said genetic antiviral agent is an antisense molecule, a ribozyme, a nucleic acid decoy, a transdominant mutant protein, a single chain antibody, a cytokine, a cellular antigen or receptor.

5. The method of claim 4, wherein said genetic antiviral agent comprises a ribozyme.

6. The method of claim 5 wherein said ribozyme is in a ribozyme cassette comprising one, two or multiple ribozymes.

7. The method of claim 6, wherein each ribozyme of said cassette cleaves a different site.

8. The method of claim 6 wherein said ribozyme cassette comprises at least two ribozymes.

9. The method of claim 4, wherein said genetic antiviral agent encodes a single-chain antibody to a protein of a wild-type virus, helper virus or helper vector.

10. The method of claim 4, wherein said genetic antiviral agent is an antisense molecule.

11. The method of claim 1, wherein said conditionally replicating vector comprises at least one second nucleotide sequence, which confers to said host cell a selective advantage over a second cell infected with a wild-type strain of virus or helper virus or helper vector, but wherein said second cell lacks said conditionally replicating vector, or confers a selective advantage to said conditionally replicating vector over said wild-type strain, helper virus or helper vector.

12. The method of claim 11, wherein said second nucleotide sequence confers multidrug resistance, encodes a mutant protease, encodes a mutant reverse transcriptase, or comprises a promoter, optionally including an enhancer, that is activated in said host cell in preference to promoters present in said wild-type virus strain, helper virus or helper vector.

13. The method of claim 11, wherein said second nucleotide sequence confers multidrug resistance and said conditionally replicating vector is used with a drug.

14. The method of claim 11, wherein said second nucleotide sequence comprises a promoter optionally, including an enhancer, that is preferentially activated in said host cell and said conditionally replicating vector is used with a cytokine.

15. The method of claim 1 wherein said conditionally replicating vector is selectively replicated over a wild-type virus, a helper virus, or a helper vector in a host cell selected from the group consisting of a hematopoietic stem cell, a fibroblast cell, an epithelial cell, a blood or blood vessel cell, a cell from the respiratory system, a cell from the gastrointestinal system, a cell from the urinary system, a cell from the nervous system, a cell from the integumentary system, and an antigen presenting cell.

16. The method of claim 15 wherein said host cell is selected from the group consisting of a lymphocyte, a macrophage, and an astrocyte.

17. The method of claim 1 wherein said first nucleotide sequence is derived from a wild-type virus.

18. A method of expressing a gene in a target cell, which method comprises:
  a) contacting the target cell with a replicated vector that has been produced in a host cell provided with:
    (i) a conditionally replicating virus vector which comprises at least one gene to be expressed and further comprises at least a first nucleotide sequence wherein:
      (a) the conditionally replicating vector is replicated in said host cell only upon complementation with a wild-type virus, a helper virus, or a helper vector; and
      (b) the conditionally replicating vector is selectively replicated over said wild-type virus, helper virus, or helper vector; and
    (ii) a wild-type virus, a helper virus, or a helper vector, wherein said wild-type virus, helper virus or helper vector is adversely affected by the presence of said first nucleotide sequence;
  or with:
    (i) a helper virus or a helper vector, which comprises at least a first nucleotide sequence, wherein said helper virus or helper vector is not adversely affected by the presence of said first nucleotide sequence; and
    (ii) a conditionally replicating virus vector which comprises at least one gene to be expressed wherein:
      (a) the conditionally replicating vector replicates in a host cell only upon complementation with a wild-type virus, a helper virus, or a helper vector; and
      (b) genetic recombination between the conditionally replicating vector and the helper virus or helper vector is reduced by the presence of said first nucleotide sequence; and
      (c) the conditionally replicated vector is selectively replicated over said helper virus or helper vector; and
  b) expressing said gene in the target cell.

19. The method of claim 18 wherein expressing said gene in said target cell inhibits replication of a wild-type strain of said virus in said cell.

20. The method of claim 18, wherein said first nucleotide sequence comprises or encodes, in which case it also expresses, a genetic antiviral agent.

21. The method of claim 20, wherein said genetic antiviral agent is an antisense molecule, a ribozyme, a nucleic acid decoy, a transdominant mutant protein, a single chain antibody, a cytokine, a cellular antigen or receptor.

22. The method of claim 21, wherein said genetic antiviral agent comprises a ribozyme.

23. The method of claim 22 wherein said ribozyme is in a ribozyme cassette comprising one, two or multiple ribozyymes.

24. The method of claim 23, wherein each ribozyme of said cassette cleaves a different site.

25. The method of claim 23 wherein said ribozyme cassette comprises at least two ribozymes.

26. The method of claim 21, wherein said genetic antiviral agent encodes a single-chain antibody to a protein of a wild-type virus, helper virus or helper vector.

27. The method of claim 21, wherein said genetic anti viral agent is an anti sense molecule.

28. The method of claim 18, wherein said conditionally replicating vector comprises at least one second nucleotide sequence, which confers to said target cell a selective advantage over a second cell infected with a wild-type strain of virus or helper virus or helper vector, but wherein said second cell lacks said conditionally replicating vector, or confers a selective advantage to said conditionally replicating vector over said wild-type strain, helper virus or helper vector.

29. The method of claim 28, wherein said second nucleotide sequence confers multidrug resistance, encodes a mutant protease, encodes a mutant reverse transcriptase, or comprises a promoter optionally including an enhancer that is activated in said host cell in preference to promoters present in said wild-type virus strain, helper virus or helper vector.

30. The method of claim 28, wherein said second nucleotide sequence confers multidrug resistance and said conditionally replicating vector is used with a drug.

31. The method of claim 28, wherein said second nucleotide sequence comprises a promoter optionally including an enhancer that is preferentially activated in said host cell and said conditionally replicating vector is used with a cytokine.

32. The method of claim 18 wherein said conditionally replicating vector is selectively replicated over a wild-type virus, a helper virus, or a helper vector in a target cell selected from the group consisting of a hematopoictic stem cell, a fibroblast cell, an epithelial cell, a blood or blood vessel cell, a cell from the respiratory system, a cell from the gastrointestinal system, a cell from the urinary system, a cell from the nervous system, a cell from the integumentary system, and an antigen presenting cell.

33. The method of claim 32 wherein said target cell is selected from the group consisting of a lymphocyte, a macrophage, and an astrocyte.

34. The method of claim 18 wherein said first nucleotide sequence is derived from a wild-type virus.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 39 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

GTGTGCCCGT CTGTTGTGTG ACTCTGGTAA CTAGAGATC     39

(2) INFORMATION FOR SEQ ID NO:2:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GTGTGCCCAC CTGTTGTGTG ACTCTGGCAG CTAGAGAAC     39

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: DNA (other nucleic acid)

(xi) SEQUENCE DESCRIPTION: SEQ ID NO:3:

CACACAACAC TGATGAGGCC GAAAGGCCGA AACGGGCACA     40

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: DNA (other nucleic acid)

(xi) SEQUENCE DESCRIPTION: SEQ ID NO:4:

ATCTCTAGTC TGATGAGGCC GAAAGGCCGA AACCAGAGTC     40

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

GTGTGCCCGC CTGTTGTGTG ACTCTGGTAA CTAGAGATC     39

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

GTGTGCCCGT CTGTTGTGTG ACTCTGGCAA CTAGAGATC     39

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:7:

TGTGACGTCG ACCACACAAC ACTGATG                            27

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:8:

TGTGACGTCG ACTCTAGATG TGCCCGTTTC GGC                    33

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:9:

GGTTAAGCTT GAATTAGCCC TTCCAGTCCC C                      31

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:10:

GGTTGGATCC GGGTGGCAAG TGGTCAAAAA G                      31

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:11:

CGGATCCACG CGTGTCGACG AGCTCCCATG GTGATCAG              38

```
(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:12:

GGTTAAGCTT GTCGCCGCCC CTCGCCTCTT G                                          31

(2) INFORMATION FOR SEQ ID NO:13:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: DNA (other nucleic acid)

(xi) SEQUENCE DESCRIPTION: SEQ ID NO:13:

AAGCTTGCCT TGAGTGCTCA AAGTAGTGTG TGCCCACCTG TTGTGTGACT CTGGCAGCTA          60

GAGATCCCAC AGACCCTTTT AGTCAGTGTG GAAAATCTCT AGCAGTGGCG CC                 112

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

GTGTGCCCNN CTGTTGTGTG ACTCTGGNAN CTAGAGANC                                  39

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

GTGTGCCCAT CTGTTGTGTG ACTCTGGTAA CTAGAGATC                                  39

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

GTGTGCCCGT CTGTTGTGTG ACTCTGGTAG CTAGAGATC                                  39
```

-continued (2) INFORMATION FOR SEQ ID NO:17:

(i) SEQUENCE CHARACTERISTICS:
        (A) LENGTH: 152 base pairs
        (B) TYPE: nucleic acid
        (C) STRANDEDNESS: double
        (D) TOPOLOGY: linear (ii) MOLECULE TYPE: DNA (other)

(xi) SEQUENCE DESCRIPTION: SEQ ID NO:17:

```
GATCGAATTC CTGCTATGTT CTGATGAGTC CGAAAGGACG AAACACCCAT TTCCCGGGTT      60

TAGGATCCTG ATGAGCGGAA AGCCGCGAAA CTGGCTCCGG CCGTTTTAGG CTCTGATGAG     120

CTGGAAACAG CGAAACTTCC TGGTCGACGA TC                                   152
```